United States Patent [19]

Cooper et al.

[11] Patent Number: 5,739,104

[45] Date of Patent: Apr. 14, 1998

[54] ANTI-FUNGAL AGENTS

[75] Inventors: Alan B. Cooper, West Caldwell; Anil K. Saksena, Upper Montclair; Dinanath F. Rane, Morganville; Edwin Jao, Iselin; Viyyoor M. Ginjavallabhan, Parsippany; Ashit Ganguly, Upper Montclair; Jagdish J. Desai, Spotswood; James Wang, Westfield, all of N.J.

[73] Assignee: Schering Corporation, Kenilworth, N.J.

[21] Appl. No.: 428,974

[22] Filed: Apr. 26, 1995

Related U.S. Application Data

[63] Continuation-in-part of Ser. No. 237,794, May 4, 1994, abandoned.

[51] Int. Cl.⁶ .................... A61K 38/12; C07K 530/317
[52] U.S. Cl. .................... 514/9; 530/323; 530/317
[58] Field of Search .................... 514/9; 530/317, 530/323

[56] References Cited

FOREIGN PATENT DOCUMENTS

| | | |
|---|---|---|
| 0352092 | 1/1990 | European Pat. Off. |
| 0443719 | 8/1991 | European Pat. Off. |
| 0500264 | 8/1992 | European Pat. Off. |
| 0510271 | 10/1992 | European Pat. Off. |
| 0581429 | 2/1994 | European Pat. Off. |

*Primary Examiner*—Cecilia J. Tsang
*Assistant Examiner*—Michael Borin
*Attorney, Agent, or Firm*—Matthew Boxer; John Maitner

[57] ABSTRACT

Compounds of the formula

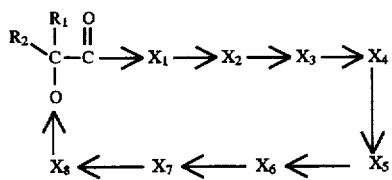

or pharmaceutically acceptable salts thereof wherein $R_1$, $R_2$, $X_1$, $X_2$, $X_3$, $X_4$, $X_5$, $X_6$, $X_7$, and $X_8$, are as set forth herein are described. These compounds are useful as agents in the treatment of fungal infections.

6 Claims, No Drawings

ANTI-FUNGAL AGENTS

This is a continuation-in-part of Ser. No. 08/237,794, filed May 4, 1994, now abandoned.

SUMMARY OF THE INVENTION

The invention relates to compounds of the formula

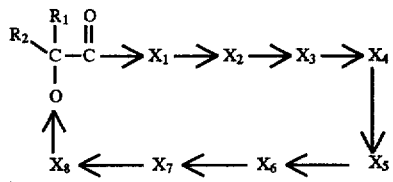

I wherein each $R_1$ and $R_2$ attached to a particular carbon is independent of each $R_1$ and $R_2$ attached to another carbon; and wherein $R_1$ is H, and $R_2$ is selected from the group consisting of

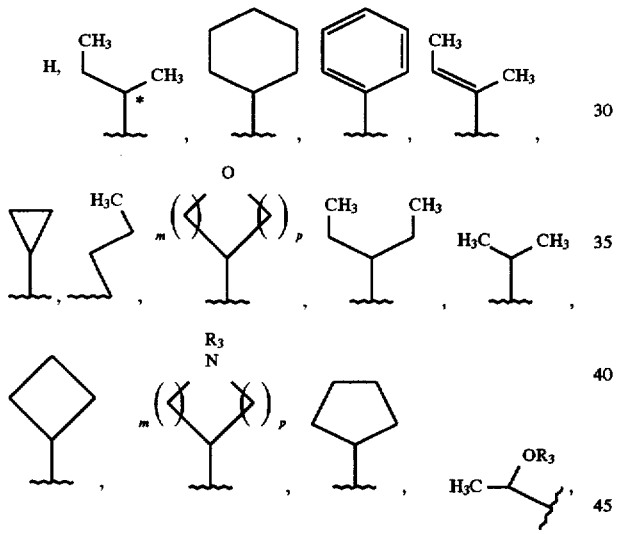

*denotes both possible isomers at this carbon center;

or $R_1$ and $R_2$ together with the carbon to which they are both attached form

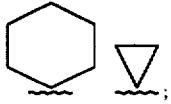

or $R_1$ and $R_2$ are both ethyl;

$R_3$ is H, methyl, ethyl, propyl or acyl;

$X_1$, and $X_6$, are independently selected from the group consisting of

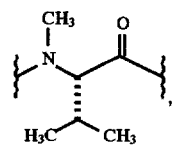

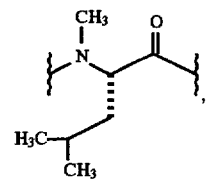

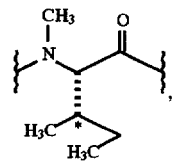

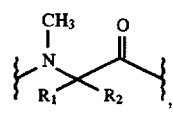

and

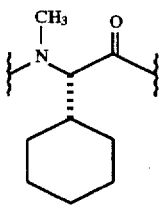

* denotes both possible isomers at this carbon center;

$X_2$ and $X_3$ each independently is selected from the group consisting of

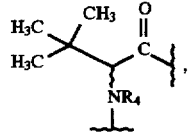

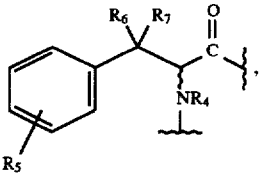

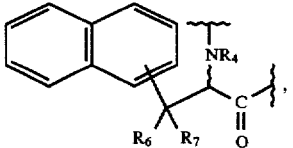

-continued

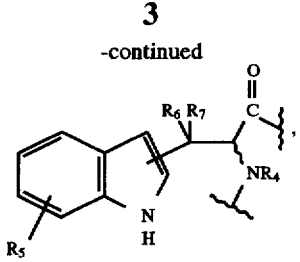

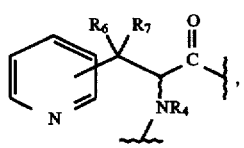

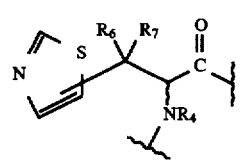

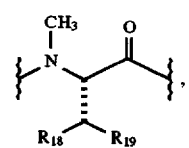

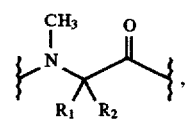

and

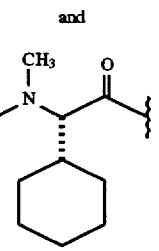

$R_4$ is H, ethyl, methyl, or propyl;
$R_5$ is H, OH, O—($C_1$–$C_3$)alkyl, Cl, F, or Br;
$R_6$ and $R_7$ are independently selected from the group consisting of H, methyl, ethyl, propyl, hydroxy, methoxy, ethoxy and propoxy;
$R_{18}$ and $R_{19}$ are independently selected from the group consisting of H, $C_1$–$C_6$ alkyl,

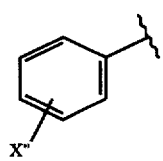

and

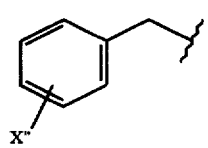

wherein X" is Cl, F, Br, OH, or $C_1$–$C_6$ alkoxy;

$X_4$ is selected from the group consisting of

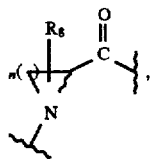

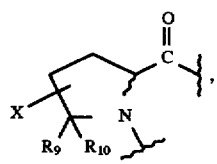

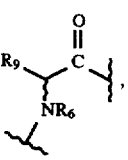

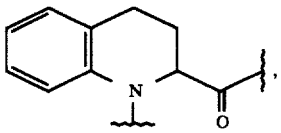

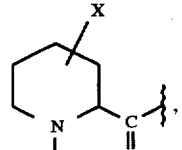

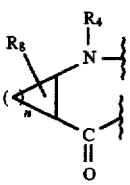

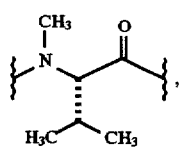

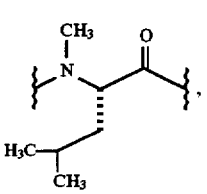

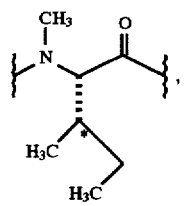

-continued

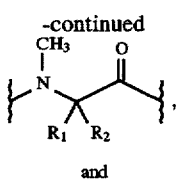

and

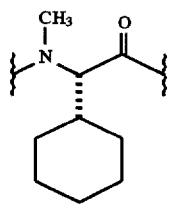

wherein X is OH or NH₂ provided that OH or NH₂ are not attached to a carbon that is attached to a heteroatom in the ring;

R$_8$ is H or C$_1$–C$_4$ alkyl;

R$_9$ and R$_{10}$ are independently selected from the group consisting of H, methyl, ethyl, or propyl;

n is 1 to 5;

m and p are independently 0 to 4 with the proviso that m+p are no greater than 4;

X$_5$ and X$_7$ are independently selected from the group consisting of

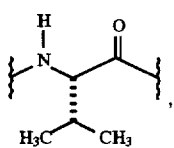

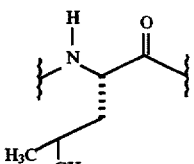

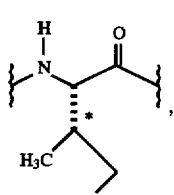

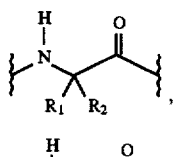

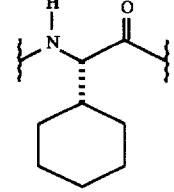

-continued

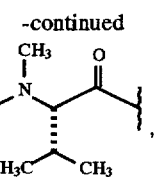

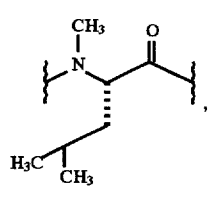

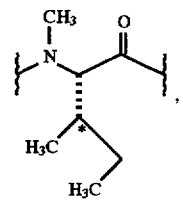

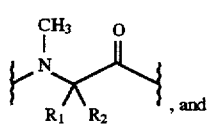, and

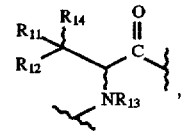

*denotes both possible isomers at this carbon center;

X$_8$ is selected from the group consisting of

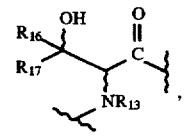

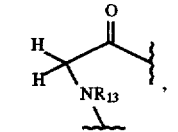

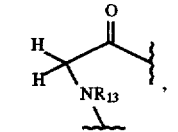

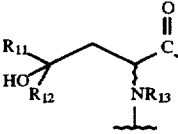

-continued

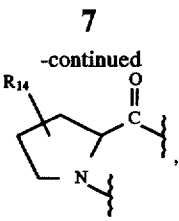

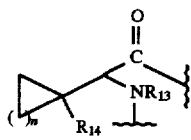

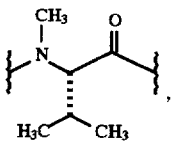

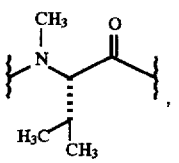

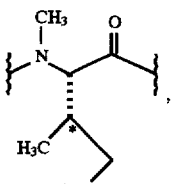

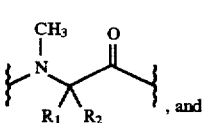, and

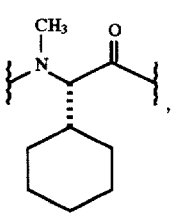, wherein $R_{11}$ is H, methyl, ethyl, propyl, or phenyl;

$R_{12}$ is H, methyl, ethyl or propyl;

$R_{13}$ is H, methyl, ethyl or propyl;

$R_{14}$ is OH, or $NHR_{15}$;

$R_{15}$ is H, methyl, or ethyl;

$R_{16}$ and $R_{17}$ are independently selected from the group consisting of H, $CF_3$, $C_1$–$C_6$ alkyl,

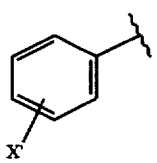

and

-continued

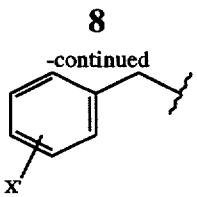

wherein X' is Cl, F, Br, OH, or $C_1$–$C_6$ alkoxy, or a pharmaceutically acceptable salt thereof when there exists in the molecule a basic group or an acid group such that a salt can form;

with the proviso that when $X_8$ is β-HO-methylvaline, $R_2$ is not

(R)-configuration and with the further proviso that $X_6$ is not D-MeVal;

and with the further proviso that when $X_8$ is threonine, and

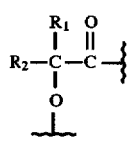

is Hmpa, n cannot be 2.

Preferred is the compound of formula I wherein $R_2$ is cyclohexyl, and $R_1$ is H.

As used herein, MeVal denotes N-methylvaline. Phe denotes phenylalanine. MePhe denotes N-methylphenylalanine. Pro denotes proline. Alle denotes alloisoleucine. Leu denotes leucine. MeThr denotes N-methylthreonine. i-Pr denotes isopropyl. n-Pr denotes n-propyl. BOP means benzotriazol-1-yloxytris (dimethylamino)phosphonium hexafluorophosphate. PyBOP means pyridyl BOP. BOP-Cl means Bis(2-oxo-3-oxazolidinyl)phosphinic chloride.

Alkyl denotes straight or branched hydrocarbon chains, which contain from 1 to 20 carbon atoms. Representative examples include methyl, ethyl, propyl, t-butyl, decyl, dodecyl and the like. Alternatively, the number of carbon atoms in a particular alkyl chain may be specified. For example, $C_1$–$C_6$ alkyl refers to an alkyl which may have one to six carbon atoms.

Alkoxy denotes —O-alkyl wherein alkyl is as described above.

As used herein Osu denotes N-oxysuccinimide, HOsu denotes N-hydroxysuccinimide. DCC denotes 1,3-dicyclohexylcarbodiimide. HOBt denotes N-hydroxybenztriazole. DMF denotes N,N-dimethylformamide. $(BOC)_2O$ denotes di-tert.butyldicarbonate. BOC denotes, tert butoxy carbonyl; and Cbz denotes benzyloxy carbonyl; and Bn denotes benzyl.

As used herein, a boldfaced bond,

◄ denotes a bond which comes up out of the plane of the page. A dashed bond, denotes a bond which comes down below of the plane of the page. A curved bond,

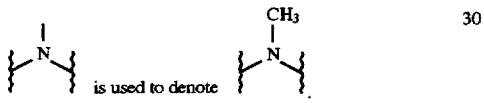

denotes a racemic mixture. As can be seen, formula I has been drawn with arrows between each of the amino acid moieties, $X_1$ through $X_8$, and between the —OC($R_1$,$R_2$)CO— portion of the molecule and between $X_1$ and $X_8$. The tail part of the arrow between the —OC($R_1$,$R_2$)CO— portion of the molecule and $X_1$ is connected to the carbonyl carbon of the —OC($R_1$,$R_2$)CO— portion of the molecule. The pointer part of the arrow between the —OC($R_1$,$R_2$)CO— portion of the molecule and $X_8$ is connected to the other oxygen of the —OC($R_1$,$R_2$)CO— portion of the molecule. The other tail parts of each arrow are connected to the acid terminus of the amino acid moiety, and the other pointer parts of each arrow are connected to the N-terminus of the amino acid moiety.

In certain chemical structures throughout this specification, "$CH_3$" has been left out for the sake of legibility, even though it is understood to be present. For example, at times the structure Additional compounds of the invention (along with physical and biological data) are:

Compounds of formula I of the invention include those, listed just below.

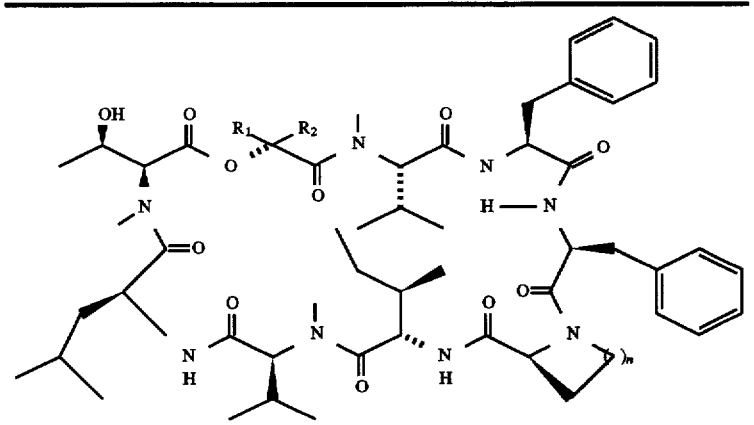

| No. | $R_2$ | n |
| --- | --- | --- |
| 1 | Cyclohexyl | 2 |
| 2 | Cyclohexyl | 1 |
| 4 | i-Pr | 2 |
| 5 | Cyclopentyl | 1 |
| 6 | Cyclopentyl | 2 |
| 7 | Phenyl | 2 |
| 8 | Cyclopropyl | 2 |
| 9 | Cyclohexyl | 3 |

In all of the compounds in the table just above, $R_1$ is H.

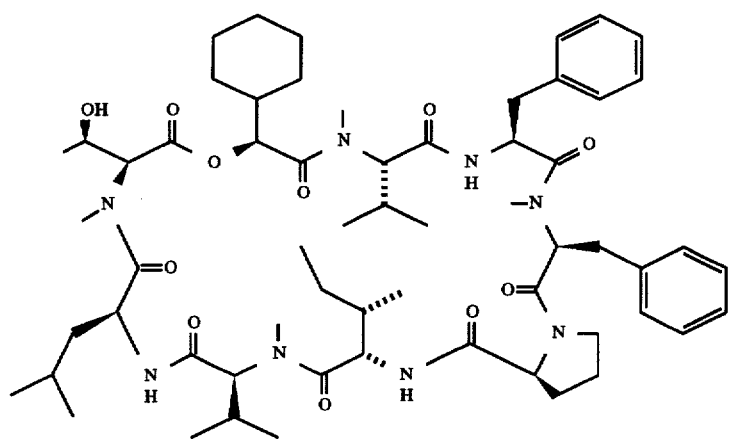
FABMS M+1=1099.5; and M+Na 1121.5. *Candida albicans* and *tropicalis* MIC=0.30.
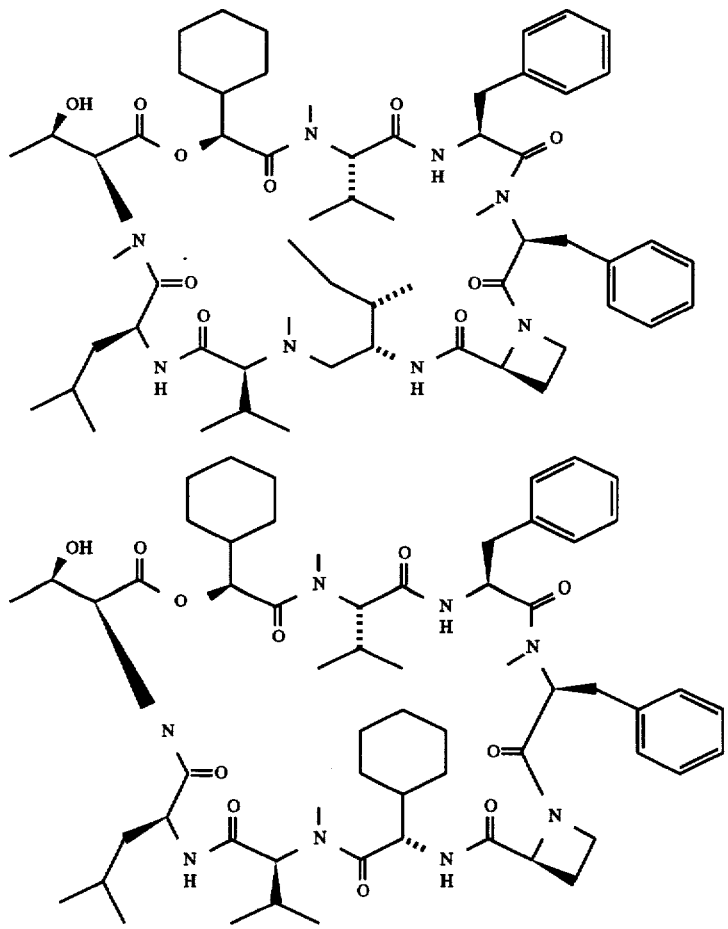
FABMS M+1=1111.5. *Candida albicans* and *tropicalis* MIC=0.16.

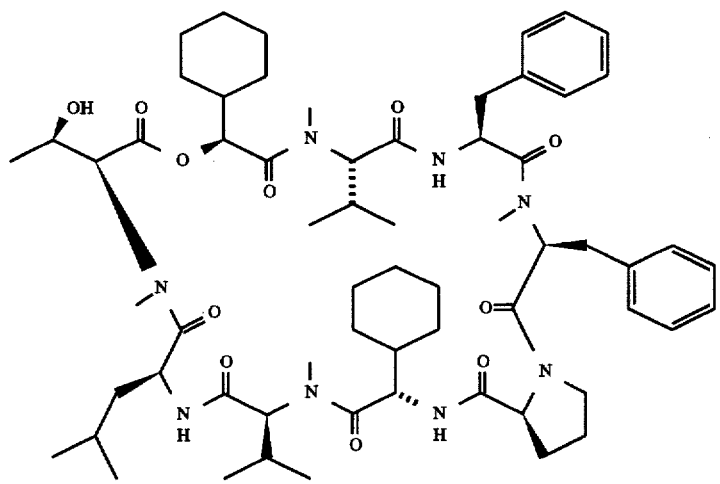

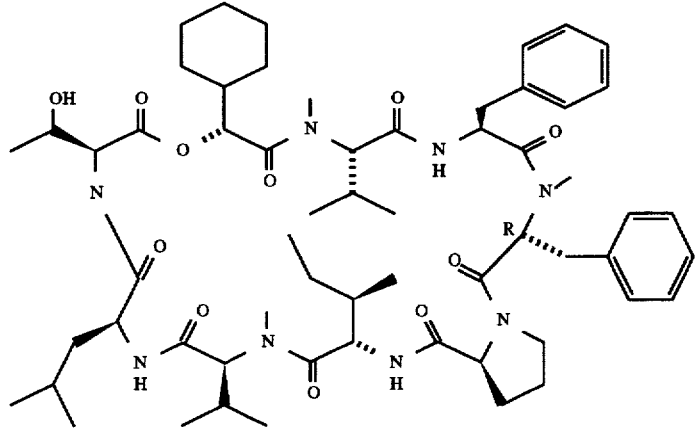

m/z (FAB), MH+ = 1113. MIC = 0.16 Ca. (SDB).

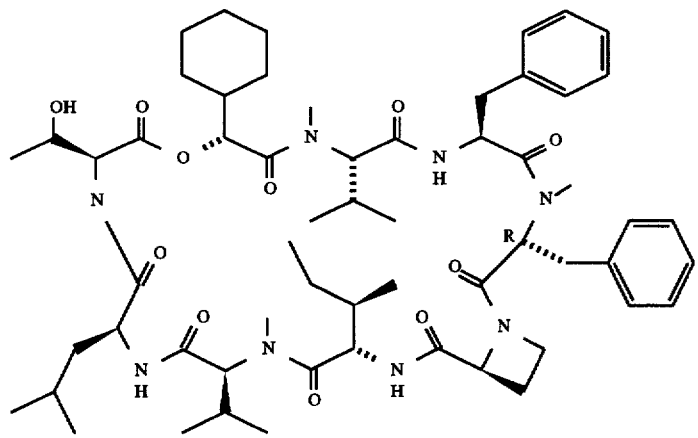

The most preferred compound of the invention is compound 1, in the table above, wherein $R_2$ is cyclohexyl or a pharmaceutically acceptable salt thereof.

The invention also relates to pharmaceutical compositions which comprises a compound of formula I in combination with a pharmaceutically acceptable carrier material.

The invention also relates to a method for treating fungi which comprises administering to a mammal in need of such treatment an anti-fungally effective amount of a compound of formula I for such purpose.

DETAILED DESCRIPTION OF THE INVENTION

Asymmetric centers exist in compounds of formula I of the invention. Accordingly, compounds of formula I include stereoisomers.

All such isomeric forms and mixtures thereof are within the scope of the present invention. Unless otherwise indicated, the methods of preparation disclosed herein may result in product distributions which include all possible stereoisomers, although it is understood that physiological response may vary according to stereochemical structure. The isomers may be separated by conventional means such as fractional crystallization, flash chromatography, or HPLC (high performance liquid chromatography).

The compounds of formula I can exist in unsolvated as well as solvated forms, including hydrated forms, e.g. the hemihydrate. In general, the solvated forms, with pharmaceutically acceptable solvents such as water, ethanol, and the like are equivalent to the unsolvated forms for the purposes of the invention.

Those compounds of formula I which have the appropriate acidic or basic functional groups, form pharmaceutically acceptable salts. The preferred pharmaceutically acceptable salts are nontoxic acid addition salts formed by adding to a compound of the invention about a stoichiometric amount of a mineral acid, such as HCl, HBr, $H_2SO_4$ or $H_3PO_4$, or of an organic acid such as acetic, propionic, valeric, oleic, palmitic, stearic, lauric, benzoic, lactic, paratoluenesulfonic, methane sulfonic, citric, maleic, fumaric, succinic and the like, respectively.

The compounds of formula I above may be prepared by the examples described below or by methods analogous to those set forth in the examples below.

The starting materials described below are known, can be prepared in accordance with known methods, or else their preparation is described herein.

under a dry inert atmosphere of, for example, argon, or, more preferably, nitrogen, in an inert, organic solvent such as tetrahydrofuran or dimethylformamide, or, more preferably, methylene chloride, at a temperature in the range of about $-20°$ C. to about 25° C., more preferably, about $-20°$ C., to obtain a compound of the formula $P_2X_2X_3OP_1$. The coupling reagent may be selected from the group consisting of BOP-Cl, DCC, BOP, or, more preferably, pivaloylchloride and N-methylmorpholine (NMM).

Completion of the reaction may be monitored by thin layer chromatography (tlc) or by other conventional means.

After the reaction is complete, the temperature is allowed to rise slowly until it reaches a temperature in the range of about $-10°$ C. to about 25° C. more preferably, about 0° C. The reaction mixture is stirred at 0° C. for about 1 to about 3 days, worked up by conventional means and isolated by conventional means such as chromatography.

The carboxylic blocking group $P_1$ is then removed from the resulting product, $P_2X_2X_3OP_1$, by reaction of $P_2X_2X_3OP_1$ in a polar, protic solvent such as methanol, propanol, or, more preferably, 200 proof ethanol with a hydrogenation catalyst such as PdOH, Pd-black, or, more preferably, 10% Pd/C, under a hydrogen atmosphere. The final product, $P_2X_2X_3OH$, may be worked up and isolated by conventional means.

REACTION SCHEME 1

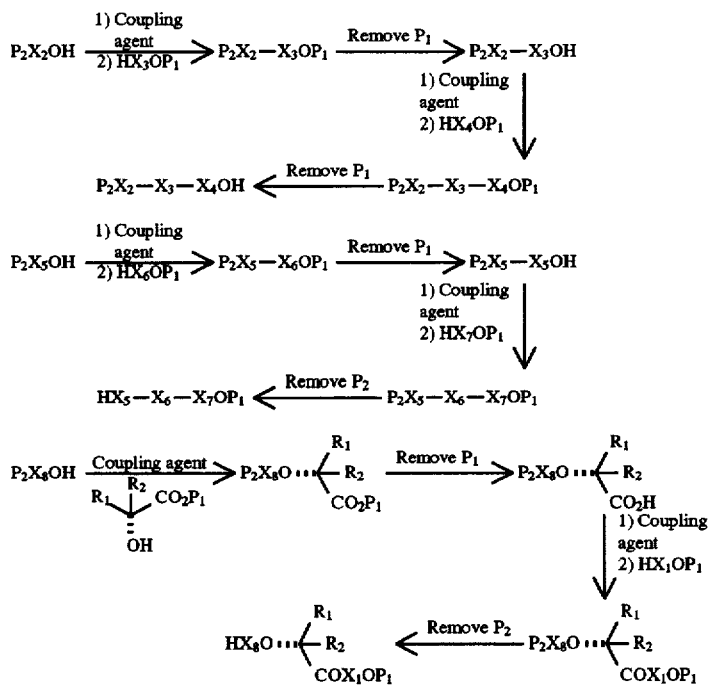

In the above reaction schemes $P_1$ is a carboxylic acid blocking group such as a methyl or benzyl ester; $P_2$ is an amine blocking group such as Boc or Cbz.; $X_1$, $X_2$, $X_3$, $X_4$, $X_5$, $X_6$, $X_7$, and $X_8$, are as described herein, and $R_1$ and $R_2$ are as described herein.

Coupling agents such as BOP, DCC, DEC and pivaloyl chloride are described below.

As shown in Reaction Scheme 1, a compound $P_2X_2OH$ is reacted with a coupling agent and a compound $HX_3OP_1$ By use of the above or analogous coupling and deprotection reactions, the conversion of $P_2X_2X_3OH$ to $P_2X_2X_3X_4OP_1$, and then to $P_2X_2X_3X_4OH$ may be carried out. Similarly, the conversion of $P_2X_5OH$ to $P_2X_5X_6OP_1$, and then to $P_2X_5X_6OH$ may be carried out. Similarly, the conversion of $P_2X_5X_6OH$ to $P_2X_5X_6X_7OP_1$. Similarly, the conversion of $P_2X_8OH$ to

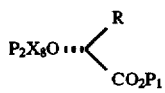

and then to

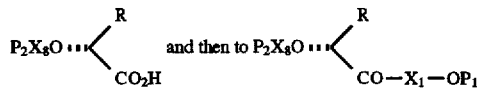

may be carried out.

To remove the amine blocking group $P_2$, so as to convert a compound of formula $P_2X_5X_6X_7OP_1$ to a compound of formula $HX_5X_6X_7OP_1$, the compound with the two protecting groups is reacted with an acid, such as trifluoroacetic acid, in aprotic, organic solvent, such as methylene chloride.

Using a similar deprotecting reaction, a compound of formula

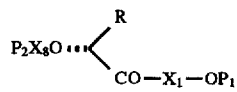

may be converted to a compound of formula

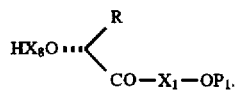

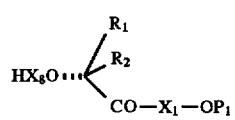

to obtain a compound of formula

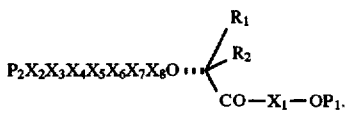

Starting with a compound of formula

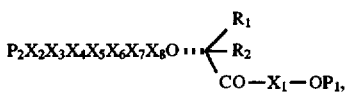

$P_1$ and $P_2$ are removed by reactions as shown above. For example, deprotection is carried out by reaction with $H_2$ over 10%Pd/C, reaction with trifluoroacetic acid in methylene chloride at a temperature in the range of about $-10°$ C. to about 25° C. more preferably, about 0° C., and then reaction with 1N HCl in dry ether.

In the same reaction vessel as the deprotection is carried out, the resulting compound of formula

REACTION SCHEME 2

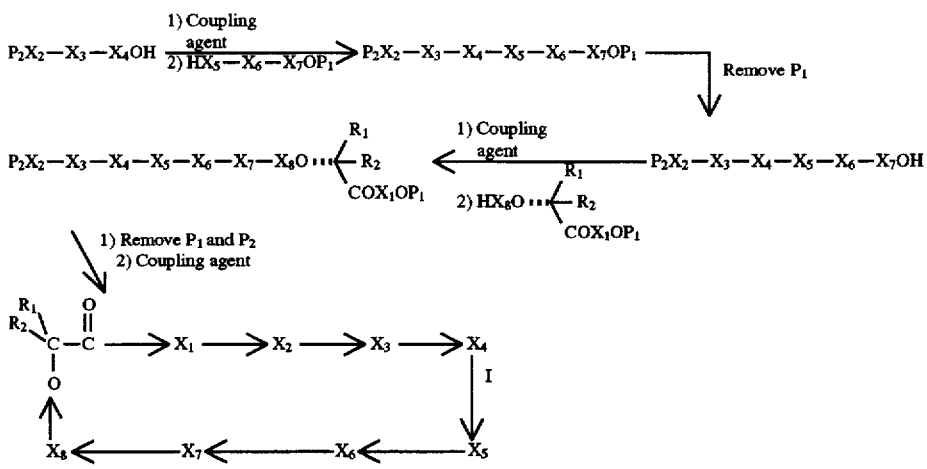

In the above reaction scheme $P_1$ is a carboxylic acid blocking group such as a methyl or benzyl ester; $P_2$ is an amine blocking group such as Boc or Cbz.; and $R_1$, $R_2$, $X_1$, $X_2$, $X_3$, $X_4$, $X_5$, $X_6$, $X_7$, and $X_8$ are as described herein, and $R_1$ and $R_2$ are as described herein.

Using the same or similar coupling reactions to those described above, and as shown in Reaction Scheme 2 just above, $P_2X_2X_3X_4OH$ may be reacted with $HX_5X_6X_7OP_1$ to obtain a compound of formula $P_2X_2X_3X_4X_5X_6X_7OP_1$ and after removal of $P_1$, it may be coupled with a compound of formula

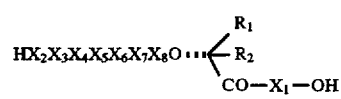

is treated with a coupling agent such as PyBrOP, DCC, or BOP-Cl more preferably, dimethylamino pyridine and benzotriazol-1-yloxytris(dimethylamino)phosphonium hexafluorophosphate (BOP), in a polar aprotic solvent such as methylene chloride or ether at a temperature in the range of about 0° C. to about 25° C. more preferably, about 25° C.

The reaction mixture is stirred for about 1 to about 3 days, and then worked up and isolated by conventional means to obtain a cyclic peptide of the formula I

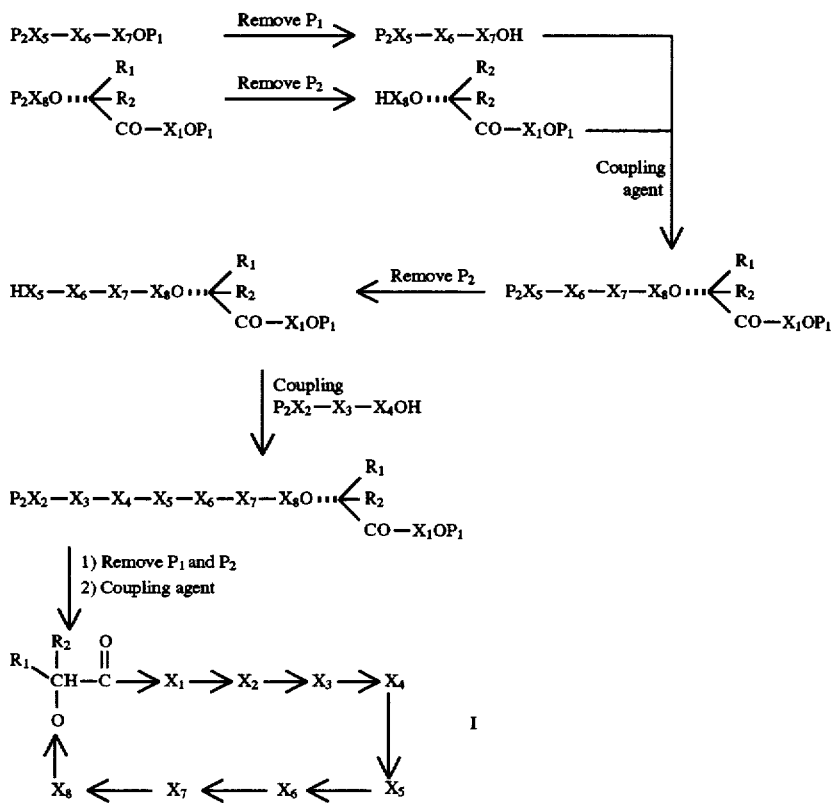

REACTION SCHEME 3

In the above reaction scheme $P_1$ is a carboxylic acid blocking group such as a methyl or benzyl ester; $P_2$ is an amine blocking group such as Boc or Cbz.; and $R_1$, $R_2$, $X_1$, $X_2$, $X_3$, $X_4$, $X_5$, $X_6$, $X_7$, $X_8$, and $X_1$, are as described herein.

Alternatively, and as shown in reaction scheme 3 just above, by using the analogous reaction conditions as are described for the coupling and deprotection reactions described above, a compound of formula $P_2X_5X_6X_7OP_1$ may be converted to a compound of formula $P_2X_5X_6X_7OH$; and a compound of formula

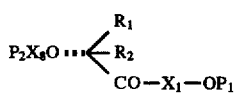

may be converted to a compound of formula

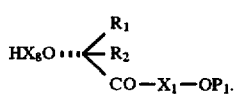

The latter two partially deprotected compounds may be coupled to form a compound of the formula

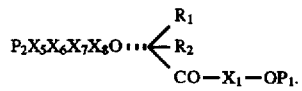

$P_2$ can be removed from this latter product to obtain a compound of the formula

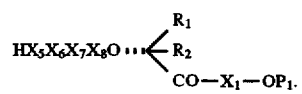

This latter compound may be coupled with a compound of the formula $P_2X_2X_3X_4OH$ (whose preparation was described above) to obtain a compound of the formula

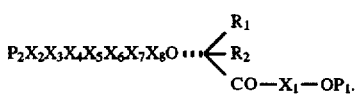

Deprotection and cyclization of the compound just above to form compounds of formula I of the invention has been described above.

Just below are given biological data for compounds of formula I of the invention.

TABLE 2

| No. | Geo. Mean MICs (μg/ml) Ca. (EMEM) | Geo. Mean MICs (μg/ml) Ca. (SDB) |
|---|---|---|
| 1 | 0.288 | 0.018 |
| 2 | 0.353 | 0.062 |
| 4 | 0.500 | 0.032 |
| 5 | 0.195 | 0.015 |
| 6 | 0.500 | 0.090 |
| 7 | 0.710 | 0.170 |
| 8 | 0.780 | 0.133 |
| 9 | 0.475 | 0.290 |

The geometric mean is taken from the following strains

Candida albicans C40
Candida albicans C41
Candida albicans C42
Candida albicans C43
Candida albicans C60
Candida albicans C79
Candida tropicalis C44
Candida tropicalis C90
Candida stellatoidea C45
Candida stellatoidea C184
Candida parapsilosis C53
Candida parapsilosis C91
Candida krusei C245
Candida krusei C246

These compounds are also active against all yeast and other opportunistic fungi.

RESULTS

The minimum inhibitory concentrations (GMMICs-R(μg/ml) for Ca (SDB) Ca (EMEM) (Derm) and (Asp) for the compounds of formula I of the invention are as shown in Table 2 above.

The minimum inhibitory concentrations were determined in accordance with the procedure set forth just below.

TEST PROCEDURES

In vitro anti-fungal activity was determined in microtiter minimum inhibitory concentration (MIC) tests using Yeast Nitrogen Broth (YNB without amino acids, Difco., Detroit, Mich.) at pH 5.4. Yeasts were grown overnight in Sabouraud Dextrose Broth at 28° C. with shaking, and concentrations adjusted in sterile saline using a spectrophoptometer at 540 mμ. Compounds were dissolved in various vehicles and diluted in media to twice the final concentrations. The Cetus Pro/Pette system was used to serially dilute 50 μl in round bottom 96 well plates (Falcon, Lincoln Park, N.J.). The turbidometrically adjusted yeast suspensions were diluted 1:3,000 in YNB. These dilutions when added to the wells, produced a final inoculum of 3×10³/ml. Plates were incubated at 37° C. for 48 hours. MICs were defined as the lowest concentrations of compound that prevented visible growth. MICs were taken against the following organisms and expressed in the table above as the geometric mean.

These compounds are active against all yeast and other opportunistic fungi.

In vivo anti-fungal activity for compounds of formula I of the invention was determined by using the test protocol set forth in Cacciapuoti et al. ANTIMICROBIAL AGENTS AND CHEMOTHERAPY, Vol.36, No. 1, January 1992, p. 64–67, which is hereby incorporated by reference. The specific test protocol used to obtain the data given below, appears in the just above mentioned article at pages 64 and 65 under the heading "C. albicans infection studies". Data obtained from this test protocol are as follows:

| Cmpd | MPK | Dosing Route | % Survival | CFUs (GM) |
|---|---|---|---|---|
| 1* | 40 | PO | 100 | 6.52 |
|  | 20 | PO | 100 | 6.38 |
|  | 10 | PO | 100 | 6.01 |
|  | 5 | PO | 70 | 6.68 |
|  | 10 | IV | 70 | 7.11 |
|  | 5 | IV | 60 | 6.90 |
| 2 | 40 | PO | 90 | 5.80 |
|  | 20 | PO | 70 | 6.50 |
|  | 10 | PO | 50 | 7.50 |
|  | 5 | PO | 50 | 7.50 |
| Vehicle* |  | PO | 40 | 8.28 |
| Vehicle |  | PO | 40 | 8.2 |

The numbering for the compounds tested is the same as the numbering used for the compounds in the rest of the application. The mice used in the above experiment were Charles River, white, male, mice weighing between 18 and 20 grams. The organism used to infect the mice was C. Albicans, C-43, 1XE6 CFU/mice, 0.1 M1 IV. The treatment was once a day for 4 days starting 4 hours post infection for those compounds which have a * next to them. For those compounds which have no * next to them, the treatment was once a day for 4 days starting 24 hours post infection. The dose was 0.1 ml/mouse in either case. The vehicle used with the compounds was Tween 80:Ethanol:PBS (1:9:40 or 2%:18%:80%)

The pharmaceutical compositions of the present invention may be formulated by combining a compound of the invention or pharmaceutically acceptable salt thereof with any suitable diluent, i.e., inert pharmaceutical carrier or diluent adapted for administration orally, parenterally, topically, vaginally or rectally.

Examples of suitable compositions include solid or liquid compositions for oral administration such as tablets, capsules, pills powders, granules, solutions, suspensions or emulsions. They may also be manufactured in the form of sterile, solid compositions which can be dissolved in sterile water, physiological saline or some sterile, injectable medium immediately before use.

Topical dosage forms may be prepared according to procedures well known in the art, and may contain a variety of ingredients, excipients, and additives. The formulations for topical use include ointments, creams, lotions, powders, aerosols, pessaries, and sprays. Of these, lotions, ointments, and creams, may contain water, oils fats, waxes, polyesters, alcohols or polyols, plus such other ingredients as fragrances, emulsifiers, and preservatives. Powders are made by mixing the active ingredient with a readily available, inert, pulverous distributing agent such as talcum, calcium carbonate, tricalcium phosphate, or boric acid. Aqueous suspensions of the above powders may also be made. Solutions or emulsions may also be prepared using inert solvents which are preferably nonflammable, odorless, colorless, and nontoxic, for example, vegetable oils, isopropanol, dimethyl sulfoxide, hydrogenated naphthalenes, and alkylated naphthalenes. Similarly, aerosol, and non aerosol sprays may be prepared using solutions or suspensions in appropriate solvents, for example, difluorodichloromethane for aerosols.

Parenteral forms to be injected intravenously, intramuscularly, or subcutaneously, are usually in the form of a sterile solution, and may contain salts or glucose to make the solution isotonic.

Compounds of the invention may also be incorporated in vaginal or rectal suppositories. Suppositories may be prepared by methods which are conventional in the art. In addition to comprising a compound of the invention, suppositories may contain a suppository base made up of biocompatible polymers, a surfactant, and an absorbent in a vegetable oil phase.

In addition, the suppositories may be further modified by inclusion of an antioxidant.

When used orally or parenterally, the compounds of the invention can be administered in an amount ranging from about 0.02 mg/kg body weight to about 40.0 mg/kg body weight, preferably from about 0.1 mg/kg body weight to about 20 mg/kg body weight per day.

Determination of the proper dosage of a compound of the invention for a particular situation is within the skill of the art. Generally, treatment is initiated with smaller dosages that are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of formula I and the pharmaceutically acceptable salts thereof will be regulated according to the judgment of the attending clinician considering such factors as age, condition, size of the patient, severity of the symptom being treated, and the pharmacokinetics of the particular compound being employed.

The invention disclosed herein is exemplified by the following preparative examples, which should not be construed to limit the scope of the disclosure. Alternative mechanistic pathways and analogous structures within the scope of the invention may be apparent to those skilled in the art.

EXAMPLE 1

Preparation of BOC-N-Methyl-Valine

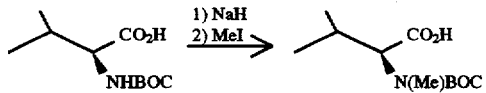

60 gm of BOC-Valine were dissolved in 1 L of dry tetrahydrofuran (THF) under a dry nitrogen atmosphere. The reaction mixture was cooled in an ice bath with overhead stirring and portionwise, 34 gm of sodium hydride(NaH) (60% oil dispersion) were added. The temperature was kept below 25° C. After the addition was complete, 141 ml of methyl iodide were added dropwise over 30 minutes. When the reaction became too viscous another 200 to 300 ml more of THF were added. After 1 hour the reaction was allowed to come to room temperature and stirred for 18 hours (overnight). A small sample was worked up by adding to water and washing the water layer with ethyl acetate. The water layer was acidified with (10%) aqueous citric acid and extracted with methylene chloride. The proton magnetic resonance spectrum (PMR) was taken and showed the correct proportion of N-methyl to valine methyls. (note: thin layer chromatography (TLC) did not show separation of starting BOC-Valine and product).

Large scale workup: an amount of water sufficient to stop the bubbling caused by excess NaH (that is, approximately 30 ml of water) was added. The THF was evaporated off to about 200 ml. 1 L of water was added and the reaction mixture was washed with 2×500 ml of ethyl acetate. The aqueous layer was acidified with solid citric acid to a pH of about 3 to 3.5. The reaction mixture was extracted with 3×500 ml of methylene chloride, dried over MgSO$_4$, filtered, and evaporated to dryness. The compound eventually crystallized as a semi-gummy tan solid. FAB-MS m/z 232 (M+H).

EXAMPLE 2

Preparation of N-methyl-Valine-O-benzyl ester hydrochloride

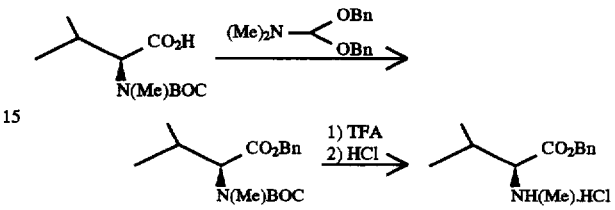

20 gm of BOC-N-methyl-valine were dissolved in 300 ml of dry toluene. 29.3 ml of DMF-dibenzylacetal were added and the reaction mixture was refluxed under a dry nitrogen atmosphere for 18 hours (overnight). TLC (30%ETOAc/ Hexanes) was used to see if reaction was complete. Until it was complete, refluxing was continued and the reaction was further monitored by TLC. When completed, the reaction mixture was evaporated to an oil. The oil was dissolved in 100 ml of methylene chloride and cooled in an ice bath. 100 ml of trifluoroacetic acid (TFA) were added and the temperature was allowed to rise slowly to room temperature. After 3 hours, the reaction was checked by TLC to see if it had gone to completion. The TLC was carried out with two solvent systems, 5% MeOH/CH$_2$Cl$_2$ and 30% EtOAc/ hexanes. When the reaction was complete, it was worked up by evaporating to an oil, adding hexanes and shaking or swirling the mixture. The supernatent hexane layer was decanted off and this step was repeated two more times. The resultant syrupy material was dissolved in 800 ml of ether and 40 ml of 4N HCl in dioxane was added, dropwise, to obtain a white precipitate. The precipitate was filtered and washed with ether, dried in a vacuum oven at 40° C. to obtain 20.56 gm of product. FAB-MS m/z 222 (M+H).

EXAMPLE 3

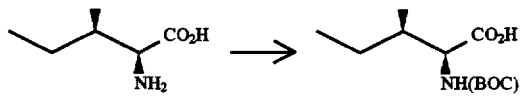

Preparation of BOC-alloisoleucine

L-allo-isoleucine (20.0 gm, 0.152 mole) was suspended in 200 ml of 50% MeOH/H$_2$O. The pH was adjusted to 9–9.5 with 4N NaOH. The reaction mixture was cooled to 10° C. and di-tert butoxydicarbonate (39.8 gm. 0.184 mole) was added. The pH was maintained at 9–9.5 with NaOH. After about 0.5 hour, the cooling bath was removed. The reaction mixture was stirred at room temperature for 3–4 hours. TLC in 5% MeOH/CH$_2$Cl$_2$ was taken. When the reaction was complete, the reaction mixture was acidified to pH 3 with 20% citric acid, extracted with 3×500 mL of CH$_2$Cl$_2$, dried over MgSO$_4$, filtered and evaporated to give a gum. 200 mL of toluene were added and the reaction mixture was evaporated. This last step was repeated two more times to obtain a gum which was dried under high vacuum for 2 days to give a solid (37.53 gm).

EXAMPLE 4

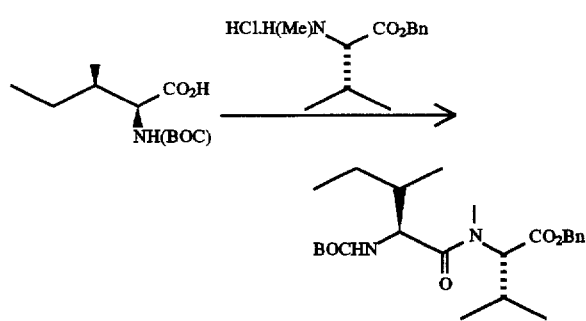

Preparation of BOC-alloisoleucyl-N-methyl-valyl-O-benzyl ester

BOC-aile (27.06 gm, 0.117 mole) was dissolved in 150 ml of dry $CH_2Cl_2$ under dry nitrogen and N-methylmorpholine (NMM) (25.73 ml, 0.234 mole) was added. The reaction mixture was cooled to −20° C., and pivaloyl chloride (15.85 ml, 0.129 mole) was added dropwise at −20° C. The reaction mixture was stirred for 4–5 hours at −20° C. Activation was checked by TLC (5% MeOH/$CH_2Cl_2$/0.5%HOAc) as follows:

(To a small aliquot, n-butylamine was added and citric acid was quickly added and the resulting mixture was shaken. TLC of $CH_2Cl_2$ layer was taken and compare with the starting BOC-aile. When the reaction was complete there was very little or no BOC-aile.) In a separate dry 250 ml round bottom flask, N-Meval-OBn HCl (30.1 g, 0.117 mole) and nmm (25.73 ml, 0.234 mole) were dissolved in 150 ml of dry $CH_2Cl_2$. The above reaction was added dropwise to this suspension at −10° to −20° C. under dry nitrogen. The temperature was allowed to slowly rise to 0° C. The reaction mixture was stirred at 0° C. for 36 hours. Completion of the reaction was checked by TLC (5% MeOH/$CH_2Cl_2$/0.5%HOAc). When the reaction was complete, the reaction mixture was washed with 20% citric acid, the $CH_2Cl_2$ layer was dried over $MgSO_4$, and filtered, and the solvent was evaporated under reduced pressure to obtain a gum (55.1 gm). The gum was dissolved in 500 ml hexane, loaded onto a flash silica column of just over 1 kg of silica packed in hexanes, and eluted first with 9 L of hexanes. 1 L fractions were collected, then eluted with 9 L of 5%EtOAc/hexanes; 9 L 7.5% EtOAc/hexanes; and finally with 9 L of 10% EtOAc/hexanes. The product containing fractions were collected and evaporated to obtain 12.5 gm of slightly impure product and 21.15 gm of pure product.

EXAMPLE 5

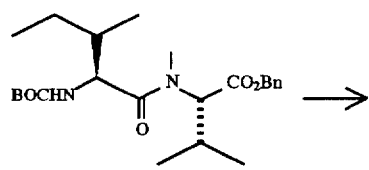

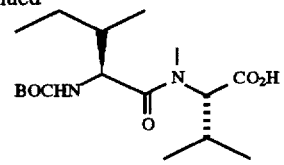

Preparation of BOC-alloisoleucyl-N-methyl-valine

BOC-alloisoleucyl-N-methyl-valyl-O-benzyl ester (21 gm, 48.3 mole) were dissolved in 200 ml of 200 proof EtOH. Under nitrogen 1.25 gm of 10% Pd/C were added and stirred under a balloon $H_2$ atmosphere. After 18 hours, the catalyst was filtered off, and the residue was washed with EtOH, and the solvent was evaporated to dryness, and azeotroped with dry toluene 3× (to get rid of the EtOH) to obtain 16.89 gm of a gummy solid. FAB-MS m/z 345 (M+H)

EXAMPLE 6

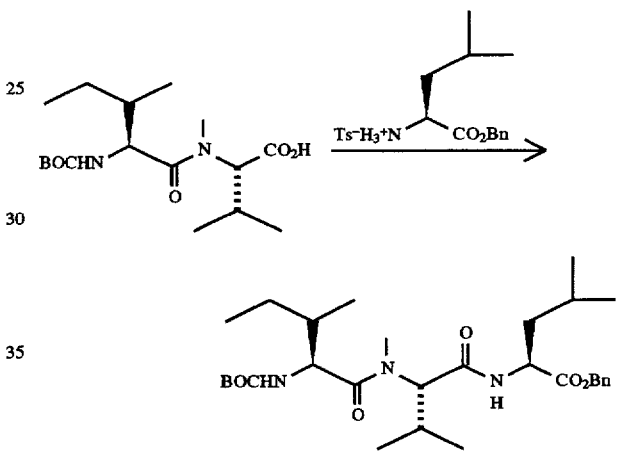

Preparation of BOC-alloisoleucyl-N-methyl-valyl-leucyl-OBn

BOC-alloisoleucyl-N-methyl-valine (16.53 gm, 48 mmole) was dissolved in 1 L of dry $CH_2Cl_2$ under dry nitrogen. L-leucine benzyl ester tosylate (94.43 gm, 240 mmol) was added, followed by the addition of nmm (26.4 ml, 240 mmol). The reaction mixture was stirred at room temperature for 5 minutes, and HOBt (14.7 gm, 96 mmol) was added. The reaction mixture was cooled to −20° C. and 1,3-dicyclohexylcarbodiimide (DCC) (18.4 gm, 96 mmol) was added in small portions over 0.5 hour so as to maintain the temperature at −20° C. After the addition was over, the reaction temperature was allowed to rise to 0° C. The reaction temperature was stirred at 0° C. overnight. TLC (5% MeOH/$CH_2Cl_2$/0.5%HOAc) and 30% EtOAc/Hexanes) was taken to see if reaction was complete. When complete, the $CH_2Cl_2$ was evaporated under vacuum to obtain an oil. The oil was dissolved in 1 L of EtOAc and washed with 1 L of 1N HCl and then with 2×1 L of distilled water (note: the reaction mixture was not allowed to remain in acidic solution long due to instability of the BOC group in acid). The reaction mixture was washed immediately with saturated $NaHCO_3$ followed by water again, dried over $Mg_2SO_4$, filtered, and evaporated to obtain a viscous syrup. The reaction mixture was chromatographed on 1.5 kg of silica gel (flash grade) by loading the compound in $CH_2Cl_2$ (~300 ml) followed by elution as follows, collecting 0.5 L fractions: 4 L hexane, 10 L 5% EtOAc/Hexanes, 16 L 7.5% EtOAc/Hexanes, 10 L 10% EtOAc/Hexanes, 10 L 12.5% EtOAc/Hexanes, 10 L 15% EtOAc/Hexanes. The compound eluted at ~10% EtOAc/Hexanes. The product containing fractions were collected and evaporated to obtain a viscous syrup (20.4 gm). FAB-MS m/z 548 (M+H)

EXAMPLE 7

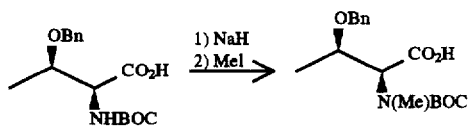

Preparation of BOC-N-methyl-O-Bn-threonine 60 gm (0.194 mol) of L-N-BOC-O-Bn-threonine were dissolved in 1 L of dry THF under a dry nitrogen atmosphere. The reaction mixture was cooled in an ice bath with overhead stirring and 23.28 gm (0.582 mol) of sodium hydride 60% oil dispersion was added, portionwise. The temperature was kept below 25° C. After the addition was complete, 141 ml of methyl iodide were added, dropwise over 30 minutes. When the reaction became too viscous another 200 to 300 ml of THF were added. After 1 hour, the reaction was allowed to come to room temperature and stirred for 18 hours (overnight). A small sample was worked up by adding to water and washing the water layer with ethyl acetate. The water layer was acidified with (10%) aqueous citric acid and extracted with methylene chloride. The PMR was taken. The PMR showed the correct proportion of N-methyl to valine methyls. (note: TLC did not show the progress of the reaction, so that PMR had to be relied upon).

Large scale workup: 30 ml of water were added dropwise. The THF was evaporated to about 200 ml. 1 L of water was added and the reaction mixture was washed with 2×500 ml of ethyl acetate. The aqueous layer was acidified with solid citric acid to a pH of about 3 to about 3.5. The aqueous layer was extracted with 3×500 ml of methylene chloride, dried over MgSO₄, filtered, and evaporated to dryness to obtain 56.4 gm of an viscous oil.

EXAMPLE 8

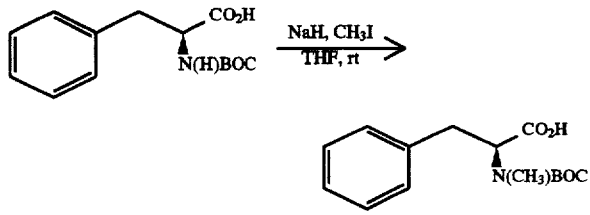

Preparation of L-N-BOC-N-Methylphenylalanine

In a dried, 3-L flask under N₂ atmosphere, L-N-BOC-Phenylalanine (70.00 g, 26.4 mmol) was dissolved in 1 L of THF. The solution was cooled in an ice bath and sodium hydride (60% oil dispersion) (31.70 g, 1.320 mol) was added to the cooled solution in portions with stirring. The viscosity increased,and approximately 350 mL more of THF were added to the flask so that the viscosity of the reaction mixture was lowered in order that the reaction mixture could be stirred again. Bubbling occurred and the reaction mixture turned gray. The mixture was stirred for 10 minutes, iodomethane (299.50 g, 2.11 mol) was added to the resulting mixture and the mixture stirred for 10 minutes at 0°–5° C. The mixture was then stirred at room temperature for 8–15 hours (overnight).

The reaction was monitored by PMR in CDCl₃. ~2 mL of the reaction mixture was taken and shaken in a mixture of CH₂Cl₂ (2 mL) and H₂O (2 mL). The aqueous layer was acidified using 10% citric acid solution (w/w) and extracted with CH₂Cl₂. The CH₂Cl₂ layer was dried (MgSO₄) and evaporated. The PMR of the residue was taken and the peak integration of N-methyl group (2.76 & 2.69 ppm) and that of phenyl group (7.10–7.40 ppm) was checked. When the ratio was less than 3 to 5, the reaction mixture was stirred for another 4 hours and the PMR of the reaction mixture was checked again. When the ratio was 3 to 5, the reaction was complete.

After the reaction was complete, 20 mL of H₂O were added to the flask slowly to destroy the excess NaH. The reaction mixture was evaporated to a syrup (most of THF was removed) and 300 mL of H₂O were added to it. The aqueous mixture was washed with CH₂Cl₂ (3×200 mL), cooled in an ice bath and acidified using citric acid solution (~160 g in 200 mL of H₂O). The pH value of the solution was checked. The acidic solution was extracted with CH₂Cl₂ (3×200 mL). The organic solution was dried (MgSO₄) and evaporated to a yellow-brown syrup (75.33 g). The syrup was seeded with crystals of L-N-BOC-N-methylphenylalanine (previously made) to obtain the crystals (a mixture of long crystals and yellow-brown oil ). This product was used for the next reaction without further purification. FAB-MS m/z 280 (M+H).

As used herein, rt means room temperature.

EXAMPLE 9

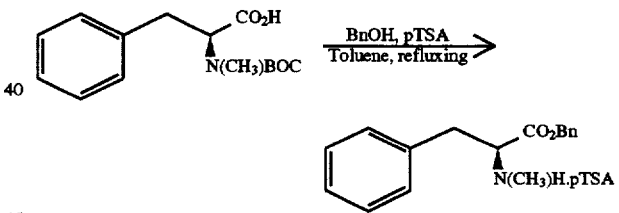

Preparation of L-N-Methylphenylalaninyl Benzyl Ester pTSA salt

L-N-BOC-N-Methylphenylalanine (40.0 g, 143 mmol), benzyl alcohol (BnOH) (68.2 g, 631 mmol) and p-toluenesulfonyl acid monohydrate (pTSA) (49.0 g, 258 mmol) were stirred in 700 ml of toluene at refluxing temperature with a Dean-Stark trap under N₂ atmosphere overnight (15 hours). The reaction mixture was allowed to cool. White solids precipitated. The solids were filtered off and rinsed with toluene. The filtrate was evaporated to a syrup. Et₂O (~300 mL) was added to the syrup and the syrup was swirled well. The Et₂O solution was seeded with a few crystals of L-N-Methylphenylalaninyl benzyl ester pTSA salt (previously made). The white precipitates were collected by filtration and the filtration cake was rinsed with cold Et₂O. The filtration cake was dried under house vacuum overnight to afford 55.05 g (87.1% yield) of L-N-Methylphenylalaninyl benzyl ester pTSA salt. The filtrate was evaporated to 100 mL and 5 mL of 4M HCl in dioxane (anhydrous) was added. A precipitate formed. The precipitate was collected by filtration and rinsed with Et$_2$O. The precipitate was dried under house vacuum to afford 2.15 g (4.93% yield) of HCl salt of L-N-Methylphenylalaninyl benzyl ester (MW, 304.84). FAB-MSm/z 270 (M+H)

Example 10

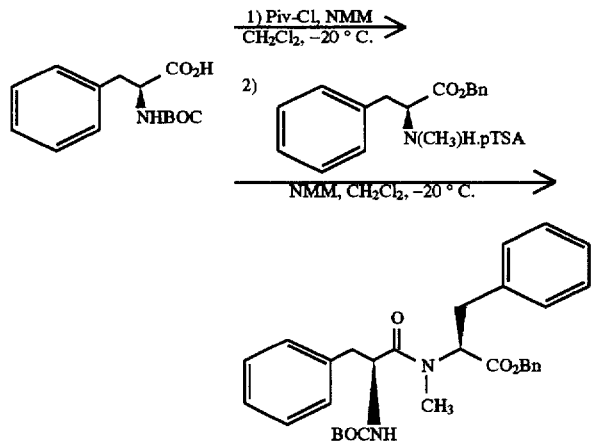

Preparation of L-N-BOC-Phenylalaninyl L-N-methylphenylalaninyl Benzyl Ester

L-N-BOC-phenylalanine (20.2 g, 76.1 mmol) and N-methylmorpholine (NMM), 16.74 mL, 152.2 mmol) were dissolved in 200 ml of CH$_2$Cl$_2$ in a dried 1-L. flask at −20° C. under N$_2$ atmosphere. Pivalonyl chloride (Piv-Cl), (9.85 mL, 79.9 mmol) was added dropwise to the solution (so as to keep the reaction mixture at −20° C.) and the reaction mixture was stirred for 4 hours at −20° C. under a N$_2$ atmosphere. After 4 hours (formation of mixed anhydride, reaction 1) the reaction mixture was checked by TLC (silica gel) by using n-butyl amine.

TLC preparation: A few drops of reaction mixture were taken and reacted with one drop of n-butyl amine. After 1 minute, 10% citric acid was added to the butyl amine adduct solution. The resulting mixture was extracted with a small amount of EtOAc. The starting material was spotted, the EtOAc layer was spotted, and these two samples were overlapped. The plate was developed in 30% of EtOAc/hexane solvent system. The disappearance of starting material and the formation of n-butyl amide was monitored. When the starting material was observed, another 5–10% of Piv-Cl was added and the reaction mixture was stirred for another 4 hours at the same reaction conditions. The reaction was then checked again by TLC until it was complete.

After the activation was complete (at least ~90–95% reaction), a mixture of L-N-methylphenylalanine p-TSA salt (21.4 g, 48.7 mmol), NMM 5.36 ml (48.7 mmol), and 200 ml of CH$_2$Cl$_2$ was added to the flask. The resultant mixture was stirred for 8 hours at −20° C. under N$_2$ atmosphere. The coupling reaction was monitored by TLC (silica gel).

TLC preparation: A few drops of reaction mixture were taken and reacted with one drop of n-butyl amine. After 2 minutes, 10% citric acid was added to the n-butyl amine adduct solution. The resultant mixture was extracted with small amount of EtOAc. A few drops of reaction mixture were then reacted with 10% citric acid. The resultant mixture was extracted with a small amount of EtOAc. These two TLC samples were compared with n-butyl amine adduct by developing the plate in 30% of EtOAc/hexane solvent system. The sample without n-butyl amine was the coupled product and the sample with n-butyl amine was the adduct of n-butyl amine. When the coupling was complete, there was no n-butyl amine adduct formation in that TLC sample. The disappearance of butyl amine adduct was also checked as this indicated the completion of the coupling reaction.

After the coupling was complete, 10% citric acid solution was added to the reaction mixture and the reaction mixture was extracted with CH$_2$Cl$_2$ (3×100 mL). The organic layer was concentrated by rotary evaporation to 200 mL. The residue was washed with saturated NaHCO$_3$ solution. The mixture was extracted with CH$_2$Cl$_2$ (3×100 mL). The organic layer was dried with MgSO$_4$. The CH$_2$Cl$_2$ filtrate was evaporated to a red-brown syrup. The product was isolated by using flash chromatography (silica gel, 18"×2"). The crude product was loaded in a minimal amount of CH$_2$Cl$_2$ to the column and the column was washed with 2 L of hexane. The column was eluted with 5% EtOAc/hexane mixture (4 L), then 10% EtOAc/hexane. The column was monitored by TLC (silica gel, 30% EtOAc/hexane).

After column purification, 23.8 g (95.0% yield) of L-N-BOC-phenylalaninyl L-N-methylphenylalaninyl benzyl ester was obtained. FAB-MSm/z 517 (M+H).

EXAMPLE 11

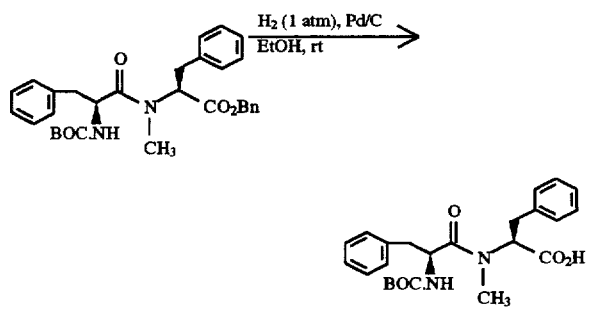

Preparation of L-N-BOC-Phenylalaninyl L-N-methylphenylalanine

L-N-BOC-phenylalanine (23.3 g, 45.0 mmol) was dissolved in 500 ml of EtOH under N$_2$ atmosphere. 2 gm of 10% palladium on activated carbon was added to the solution. The flask was equipped with a H$_2$ balloon and the flask was evacuated using the house vacuum. The H$_2$ was released to the flask and the flask was evacuated. This procedure was repeated twice. The black mixture was stirred under H$_2$ at room temperature overnight (15 hours).

The mixture was filtered through celite under N$_2$ atmosphere. The celite was rinsed with hot EtOAc under N$_2$ atmosphere. The filtration cake was saved until all the product had been recovered (the final product tended to crystallize during the hydrogenalysis). The filtrate was evaporated to dryness to obtain 16.5 g (86.0% yield) of white, foaming L-N-BOC-phenylalaninyl L-N-methylphenylalanine. The reaction was monitored by TLC (silica gel, ETOAc/hexane). FAB-MSm/z 427 (M+H).

EXAMPLE 12

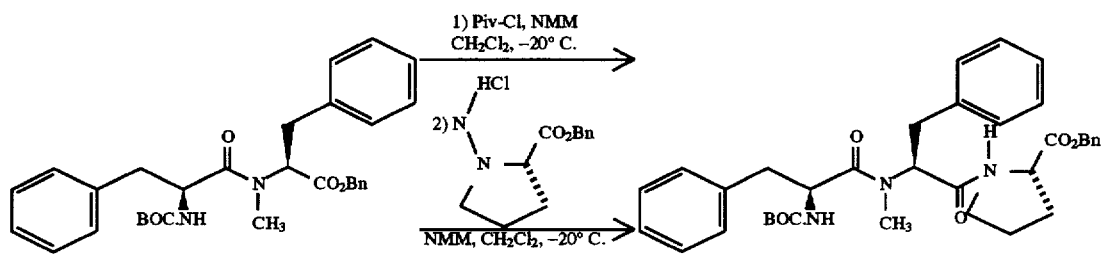

Preparation Of L-N-BOC-Phenylalaninyl L-N-methylphenylalaninyl L-prolinylBenzyl Ester L-N-BOC-phenylalaninyl L-methylphenylalanine (16.6 g, 39.0 mmol), and N-methylmorpholine (8.57 mL, 78.0 mmol) were dissolved in 200 ml of $CH_2Cl_2$ in a dried 1-L flask at −20° C. under $N_2$ atmosphere. Pivalonyl chloride (8.57 mL, 42.9 mmol) was added dropwise to the solution (so as to keep the reaction temperature at −20° C.) and the reaction mixture was stirred for 8 hours at −20° C. under $N_2$ atmosphere. During the activation (formation of mixed anhydride, reaction 1) TLC (silica gel) using n-butyl amine was used to check the reaction mixture.

TLC preparation: A few drops of reaction mixture; were reacted with one drop of butyl amine. After 2 minutes, 10% citric acid was added to the butyl amine adduct solution. The resultant mixture was extracted with a small amount of EtOAc. The L-N-BOC-phenylalaninyl L-methylphenylalanine and the EtOAc layer were spotted and these two samples were overlapped. The plate was developed in 30% of EtOAc/hexane and in 5% MeOH/$CH_2Cl_2$ (with 0.1% HOAc) solvent systems. The disappearance of L-N-BOC-phenylalaninyl L-methylphenylalanine and the formation of butyl amine adduct was monitored. When L-N-BOC-phenylalaninyl L-methylphenylalanine was observed, another 5–10% of Piv-Cl was added and the reaction mixture was stirred for another 4 hours at the same conditions. Then reaction mixture was checked again by TLC.

After the activation was complete (at least ~90–95% reaction), a mixture of L-prolinyl benzyl ester hydrochloride salt (9.4 g, 39.0 mmol), NMM (4.28 mL,39.0 mmol) and 200 ml of $CH_2Cl_2$ was added to the flask. The resulting mixture was stirred for 24 hours at −20° C. under $N_2$ atmosphere. The coupling reaction was monitored by TLC (silica gel).

TLC preparation: A few drops of reaction mixture were reacted with one drop of butyl amine. After 2 minutes, 10% citric acid was added to the butyl amine adduct solution. The resulting mixture was extracted with a small amount of EtOAc. A few drops of reaction mixture were reacted with 10% citric acid. The resulting mixture was extracted with a small amount of EtOAc. These two TLC samples were compared with L-prolinyl benzyl ester hydrochloride salt by developing the plate in 30% of EtOAc/hexane and in 5% MeOH/$CH_2Cl_2$ (with 0.1% HOAc) solvent systems. The sample without butyl amine was the coupling product and the sample with butyl amine was the adduct of butyl amine. When the coupling was complete, there was no butyl amine adduct formation in that TLC sample. The disappearance of L-prolinyl benzyl ester hydrochloride salt was also checked as the coupling reaction neared completion.

After the coupling was complete, 10% citric acid solution was added to the reaction mixture and the reaction mixture was extracted with $CH_2Cl_2$ (3×100 mL). The organic layer was washed with saturated $NaHCO_3$ solution and the organic layer was washed with brine. The organic layer was dried with $MgSO_4$, and the $CH_2Cl_2$ filtrate was evaporated to a yellow, foaming solid (24.6 g). FAB-MSm/z 614 (M+H).

EXAMPLE 13

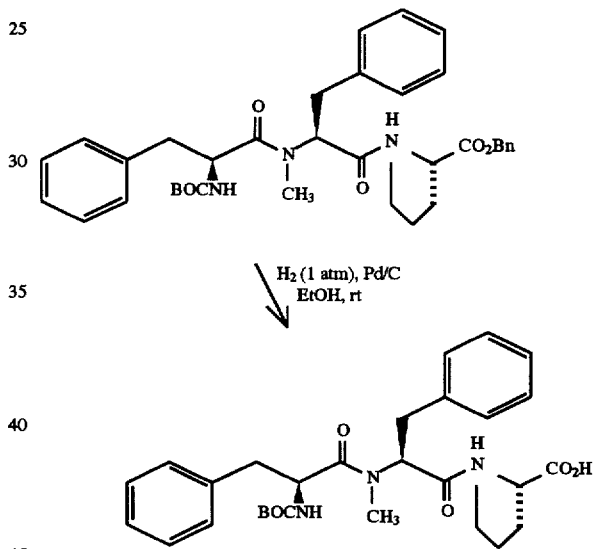

Preparation of L-N-BOC-Phenylalaninyl L-N-methylphenylalaninyl L-proline

L-N-BOC-phenylalaninyl L-N-methylphenylalaninyl L-prolinyl benzyl ester (16.9g, 27.6 mmol) was dissolved in 300 ml of EtOH under $N_2$ atmosphere. 10% Palladium on activated carbon was added to the solution. The flask was equipped with a $H_2$ balloon and the flask was evacuated using the house vacuum. The $H_2$ to the flask was released and evacuated. This procedure was repeated twice. The black mixture was stirred under $H_2$ at room temperature overnight (20 hours). The reaction mixture was filtered through Celite and the filtrate was evaporated to obtain 14.6 g of white, foaming L-N-BOC-phenylalaninyl L-N-methylphenylalaninyl L-proline. The reaction was monitored by the TLC (silica gel, 5% MeOH/$CH_2Cl_2$ with 0.1% HOAc). FAB-MSm/z 524 (M+H).

EXAMPLE 14

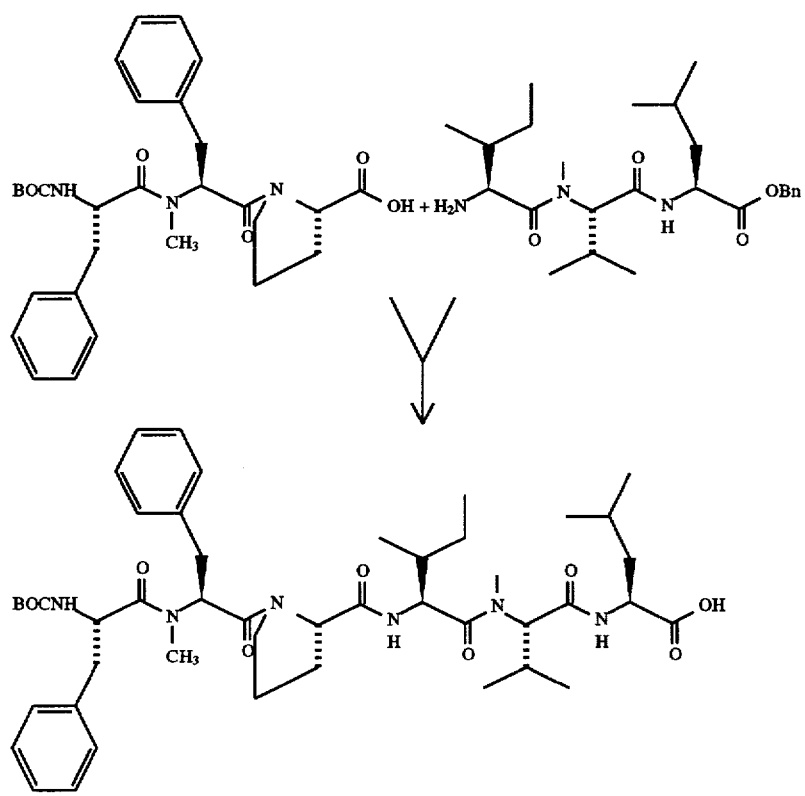

Preparation of Boc-phenylalaninyl-methylphenylalaninyl-prolyl-alloisoleucyl-methylvalyl-leucyl-benzylester L-N-BOC-phenylalaninyl L-N-methylphenylalaninyl L-proline (20 gm, 38.2 mmol) was dissolved in 200 ml of dry methylene chloride under a dry nitrogen atmosphere. NMM (8.8 ml, 80.22 mmol) was added and the reaction mixture was cooled to −20° C. Pivaloylchloride (5 ml, 40.11 mmol) was added and the reaction mixture was stirred for 18 hours at −20° C. In a separate flame dried 500 ml round bottom flask, alloisoleucyl-N-methyl-valyl-leucyl-O-benzyl ester (21.54 gm, 38.2 mmol) was dissolved in 200 ml of dry methylene chloride and 4.6 ml (42.02 mmol) of NMM. This clear solution was added to the above reaction and stirred at −20° C. for 48 hours. The cold bath was removed and, while cold, the reaction mixture acidified with 10% citric acid to pH=3 to 2.5. The reaction mixture was extracted with 3×500 ml of methylene chloride. The methylene chloride extracts were dried over magnesium sulfate, filtered, and evaporated to dryness. The resulting gum was chromatographed on a 1.25 kg flash grade silica column packed in hexanes; and eluted with 3 L hexanes, followed by 9 L 25% ethylacetate/hexanes, followed by 9 L of 30% ethylacetate/hexanes, followed by 9 L of 40% ethylacetate/hexanes, followed by 30 L of 50% ethylacetate/hexanes, and finally 9 L of 70% ethylacetate/hexanes. The product containing fractions were collected and evaporated to dryness to obtain 29.03 gm of title product.

EXAMPLE 15

Benzyl (R)-hexahydromandelic acid

Cesium carbonate (20% aqueous solution) was added to a solution of (R)-hexahydromandelic acid (3 g, 19 mmol) in 70 ml each of $H_2O$ and methanol until the pH of the solution was 7.0. All solvents were removed in vacuum. The residue was dissolved in dry DMF, evaporated to dryness, and the procedure was repeated once. The so obtained residue was re-dissolved in 70 ml of dry dimethyl sulfoxide (DMSO). Benzyl bromide (2.4 ml, 19.6 mmol) was added at ambient temperature and the solution was stirred for 4 hours. The mixture was partitioned between $H_2O$ and ethyl acetate. The organic layer was washed sequentially with $H_2O$ (twice) and brine, dried over $Na_2SO_4$ and concentrated. The residue was chromatographed on silica gel (5% EtOAc/hexane) to provide ester (4.47 g, 95%) as a white solid: $[\alpha]^{25}_D$+2.46 ($CHCl_3$); FAB-MS m/z 248 (M+H)$^+$.

EXAMPLE 16

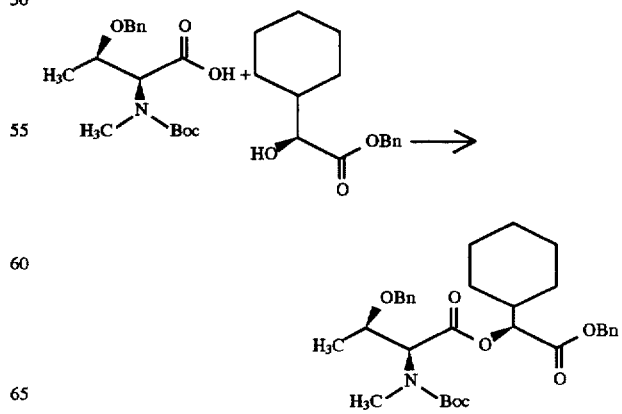

35
L-O-Bn-N-Boc-threonyl-(R)-hexahydromandelic acid-O-benzyl ester

To a stirred solution of N-Boc-O-benzyl-N-methylthreonine (13.3 g, 41.2 mmol), benzyl ester (9.9 g, 40 mmol) and 4-(N,N-dimethylamino)pyridine (4.88 g, 40 mmol) in 200 ml of dry $CH_2Cl_2$, 1,3-dicyclohexylcarbodiimide (8.73 g, 42.4 mmol) was added at 0° C. The temperature was kept at 0° C. for 5 hours, then slowly brought to 20° C. overnight. The urea was removed by filtration, and the filtrate was partitioned between 1% citric acid and ethyl acetate. The organic layer was washed with $H_2O$, brine, dried over $Na_2SO_4$ and concentrated. The residue was chromatographed on silica gel (20% isopropyl ether/hexane) to provide depsi dipeptide (18.2 g, 82%) as an oil: $[\alpha]^{25}_D$+20.61 ($CHCl_3$); FAB-MS m/z 248 (M+H)$^+$.

EXAMPLE 17

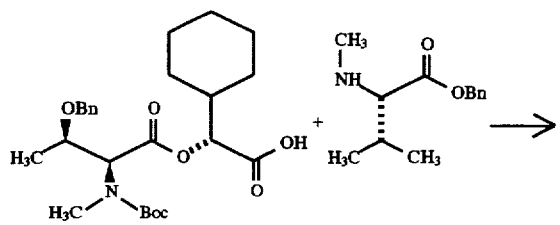

36

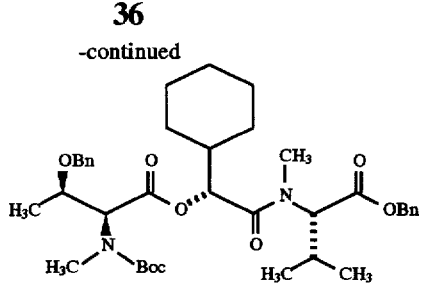

L-O-Bn-N-Boc-threonyl-(R)-hexahydromandelate-L-methyvaline-O-benzyl ester

The depsidipeptide in 95% ethanol was hydrogenated under 1 atmosphere of $H_2$ over 10% Pd/C (3% w/w) for 4 hours to generate free acid. To a stirred solution of this free acid (11.57 g, 25 mmol), N-methyl-O-benzyl-valine (6.63 g, 30 mmol) and N,N-diisopropylethylamine (9.56 ml, 55 mmol) in 150 ml of dry $CH_2Cl_2$ was added bis(2-oxo-3-oxazolidinyl)-phosphinic chloride (7.65 g, 30 mmol) at 0° C. The mixture was stirred at 0° C. for 24 hours, then partitioned between 1% citric acid and ethyl acetate. The organic layer was washed with $H_2O$, brine, dried over $Na_2SO_4$ and concentrated. The residue was chromatographed on silica gel (15% ethyl acetate/hexane) to provide depsi-tripeptide (12.36 g, 74%) as an oil: $[\alpha]_{25}^D$–37.8 ($CHCl_3$); FAB-MS m/z 667 (M+H)$^+$.

EXAMPLE 18

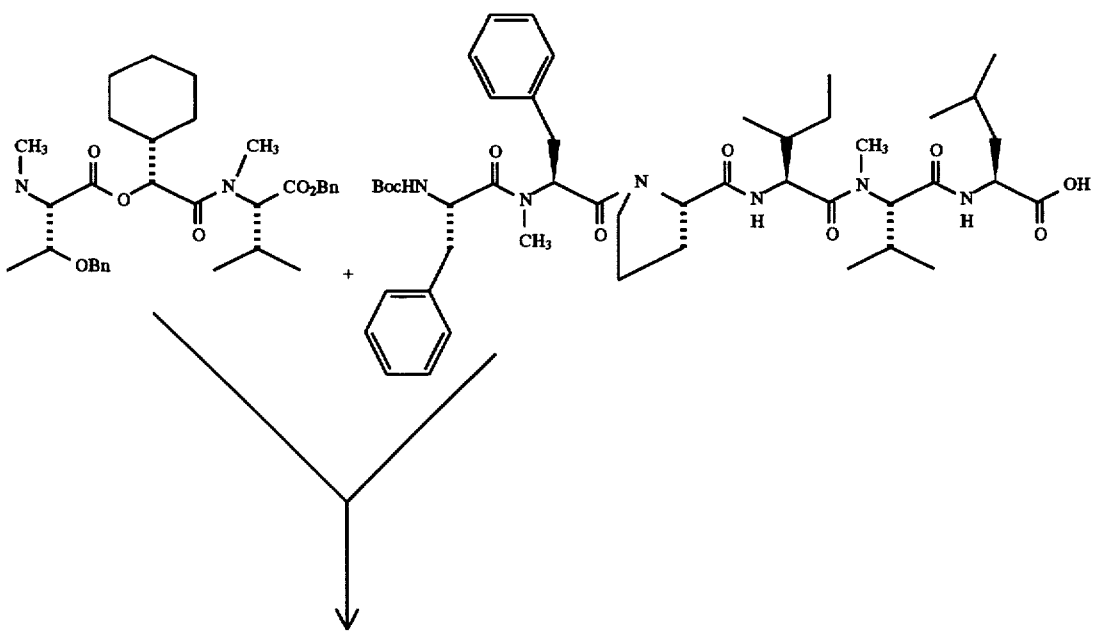

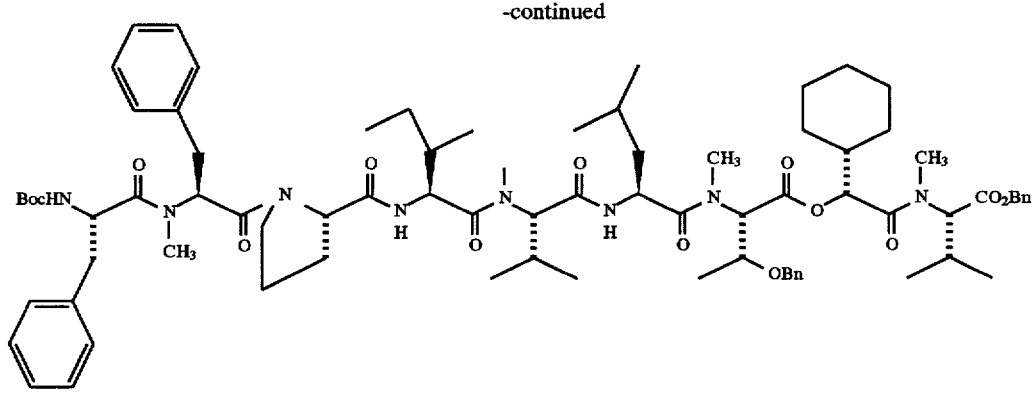

N-Boc-phenylanalyl-N-methylphenylanalyl-prolyl-allo-isoleucyl-N-methylvalyl-leucyl-L-O-Bn-threonyl-(R)-hexahydromandelate-L-methyvaline-O-benzyl ester To a solution of N-Boc-phenylanalinyl-N-methylphenylanalinyl-prolinyl-allo-isoleucinyl-N-methylvalinyl-leucine (4.9 g, 5.68 mmol) and 4-methylmorpholine (1.37 ml, 12.5 mmol) in 90 ml of dry $CH_2Cl_2$ was added trimethylacetyl chloride (0.77 ml, 6.25 mmol) at −20° C. It was stirred at this temperature overnight. The free base of depsitripeptide (3.8 g, 6.7 mmol, obtained by treating depsitripeptide with trifluoroacetic acid in $CH_2Cl_2$ at 0° C. then with saturated $NaHCO_3$) in 15 ml of $CH_2Cl_2$ was added. The solution was stirred at 0° C. for 18 hours and at ambient temperature for 3 days. It was partitioned between 1% citric acid and ethyl acetate. The organic layer was washed with $H_2O$, brine, dried over $Na_2SO_4$ and concentrated. The residue was chromatographed on silica gel (2% $CH_3OH/CH_2Cl_2$) to provide depsi-nonapeptide (4.24 g, 61%) as an oil: $[\alpha]^{25}_D$ −104 ($CHCl_3$); FAB-MS m/z 1411 (M+H)$^+$.

EXAMPLE 19

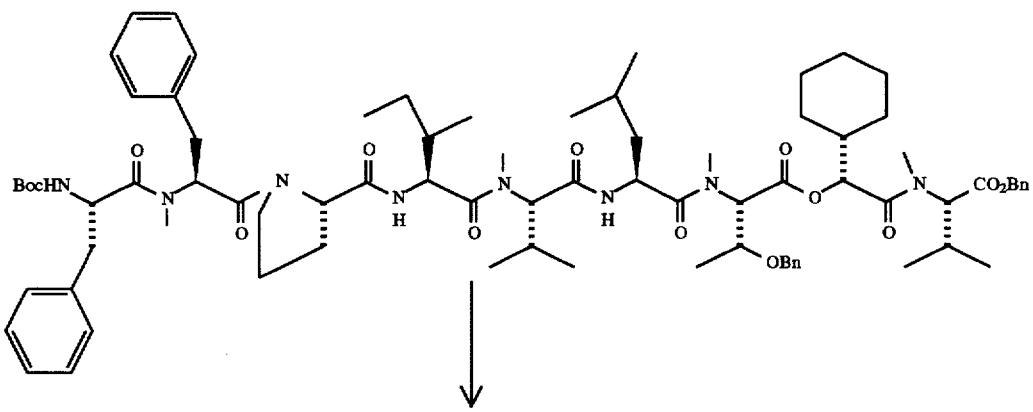

-continued

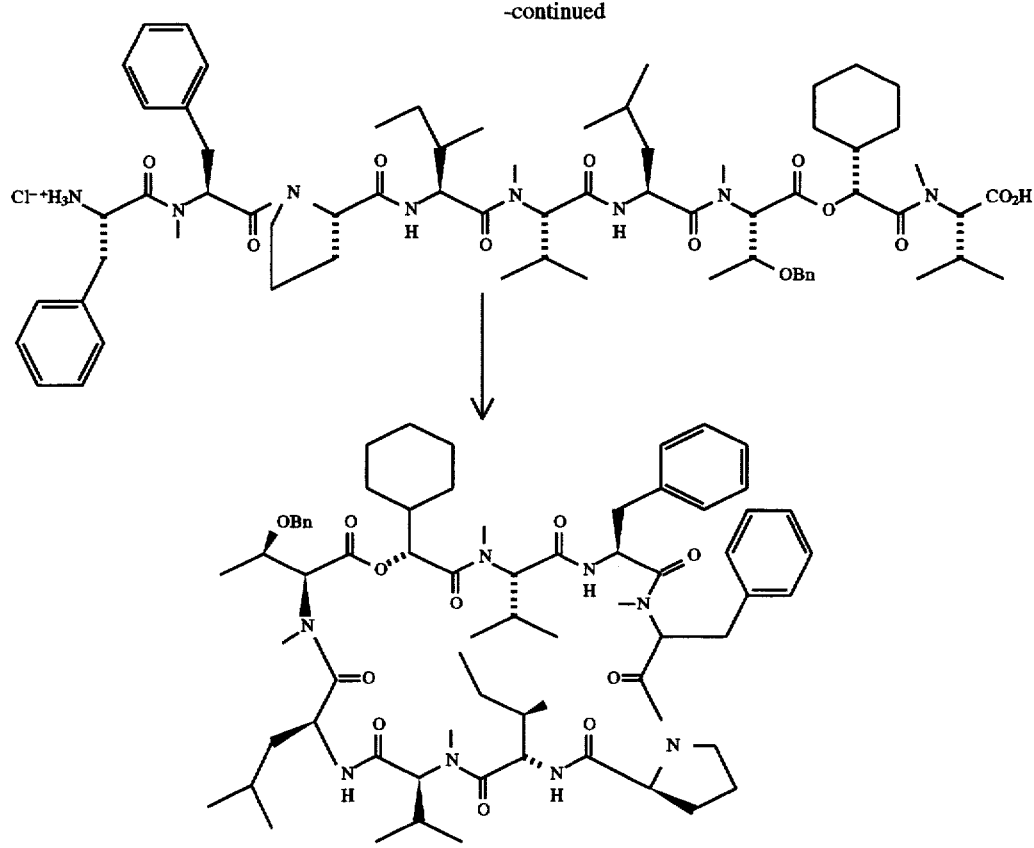

Cyclo-depsi-N-methyl-O-benzyl-threonyl-(2-hydroxyl-2-cyclohexylacetyl)-N-methylvalyl-phenylanalyl-N-methylphenylanalyl-prolyl-allo-isoleucyl-N-methylvalyl-leucine To a solution of the double deprotected depsi-nonapeptide HCl salt (3.5 g, 2.79 mmol, obtained by sequentially treating protected depsi-nonapeptide with 1 atmosphere (atm) of $H_2$ over 10% Pd/C (3% w/w), trifluoroacetic acid in $CH_2Cl_2$ at 0° C. then with 1N dry HCl in ether) in 2.5 L of dry $CH_2Cl_2$ were added dimethylaminopyridine (2.03 g, 16.71 mmol) and benzotriazol-1-yloxytris(dimethylamino)phosphonium hexafluorophosphate (BOP) (6.16 g, 13.93 mmol). The mixture was stirred for 3 days, then partitioned between 1% citric acid and ethyl acetate. The organic layer was washed with $H_2O$, brine, dried over $Na_2SO_4$ and concentrated. The residue was chromatographed on silica gel (60% ethyl acetate/hexane) to provide O-benzyl-cyclo-depsi-nonapeptide (0.52 g, 16%) as a white solid: $[\alpha]^{25}_D$ –166 ($CHCl_3$); FAB-MS m/z 1203 (M+H)$^+$.

EXAMPLE 20

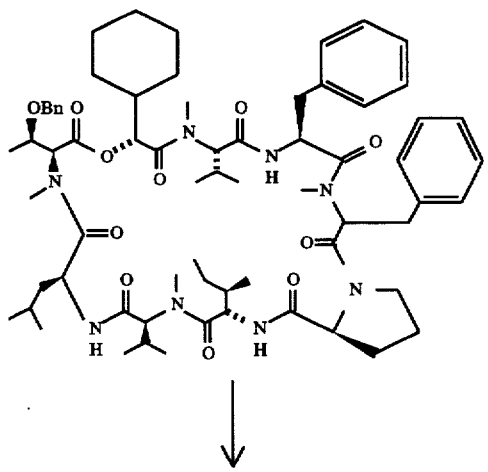

-continued

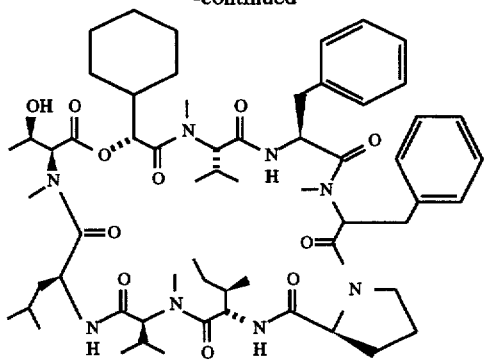

Cyclo-depsi-N-methyl-threonyl-(2-hydroxyl-2-cyclohexylacetyl)-N-methylvalyl-phenylanalyl-N-methylphenylanalyl-prolyl-allo-isoleucyl-N-methylvalyl-leucine The O-benzyl-cyclo-depsi-nonapeptide (500 mg, 0.416 mmol) in 20 ml of ethanol and 0.83 ml of 1N HCl was hydrogenated (1 atm of $H_2$, 120 mg of 10% Pd/C) for 6 hours. After Pd/C was removed and the solvents were evaporated, the crude product was chromatographed on silica gel (80% ethyl acetate/hexane) to provide cyclo-depsi-nonapeptide (302 mg, 65%) as a white solid: $[\alpha]^{25}_D$ (CHCl$_3$); FAB-MS m/z 1113 (M+H)$^+$. HRMS(FAB) calcd for $C_{61}H_{93}N_8O_{11}$ (M+H)$^+$ 1113.6964, found 1113.6944.

EXAMPLE 21

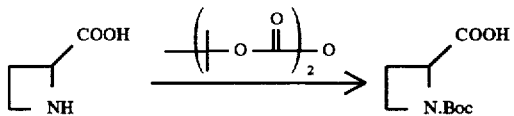

Preparation of L-N-BOC-Azetidine-2-Carboxylic Acid

L-azetidine-2-carboxylic acid (5 gm, 0.00495 mole) was suspended in 50 ml of 50% MeOH/H$_2$O. The pH was adjusted to 8 with 4N NaOH. The reaction mixture was cooled to 10° C. and di-t-butyldicarbonate (11.33 gm., 0.00519 mole) was added. The pH was maintained at 9–9.5 with NaOH. After about 0.5 hour, the cooling bath was removed. The reaction mixture was stirred at room temperature for 3–4 hours. TLC was taken in 5% MeOH/CH$_2$Cl$_2$. When the reaction was complete, the reaction mixture was acidified to pH 3 with 10% citric acid, and extracted with 3×150 ml of EtOAc, dried over MgSO$_4$, filtered and evaporated to give a semi-crystalline compound (9.9 gm.) FAB m/z 292 (M+H)$^+$.

EXAMPLE 22

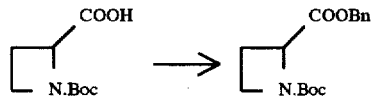

Preparation of L-N-Boc-Azetidine-2-Carboxylicacid benzyl ester

L-N-Boc-azetidine-2-carboxylic acid (9.0 gm., 0.045 mole) was dissolved in dry dimethylformamide (DMF) (90 ml) and stirred with cesium carbonate (21.87 gm., 0.067 mole) for 0.5 hour. Benzyl bromide (7.98 ml., 0.067 mole) was added and the reaction mixture was stirred overnight at room temperature. The reaction was checked for completion by TLC in 40% EtOAc/Hexane. The reaction mixture was concentrated to about 20 ml., extracted with EtOAc .(3×150 ml.) washed with 10% citric acid and brine, dried over MgSO$_4$ and evaporated to dryness to give a gum (12.78 gm.) FAB m/z292 (M+H)$^+$.

EXAMPLE 23

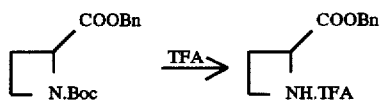

Preparation of L-azetidine-2-carboxylic acid benzyl ester TFA salt 10 gm of L-N-Boc azetidine-2-carboxylic acid benzyl ester were dissolved in CH$_2$Cl$_2$ (100 ml) and cooled to 10° C. 15 ml of TFA was added and the reaction mixture was stirred for 3 hours. TLC was taken to check for disappearance of starting material. The reaction mixture was evaporated to dryness and azeotroped with dry toluene to give an oil. 10.2 gm.

EXAMPLE 24

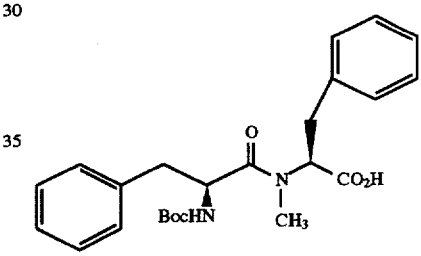

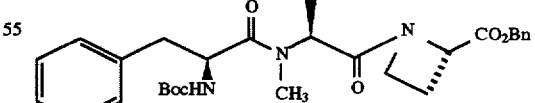

Preparation of L-N-Boc-Phenylalaninyl L-N-methylphenylalaninyl L-azetidinyl Benzyl ester Reagents
wt. (MW, mmole)
1) 1 L-N-BOC-Phenylalaninyl L-methylphenylalanine 2.16 g (426.61, 5.06)

2 N-methylmorpholine (NMM), d=0.920 1.12 mL (101.15, 10.12)
3 Pivalonyl chloride (Piv-Cl), d=0.979 0.69 mL (120.58, 5.56)
4 $CH_2Cl_2$ 30 mL 2) 5 L-Azetidinyl Benzyl Ester TFA salt 1.55 g (305.0, 5.06)
6 NMM 0.56 mL (101.15, 5.06)
7 $CH_2Cl_2$ 25 ml 1 and 2 were dissolved $CH_2Cl_2$ in a dried 1-L flask at −20° C. under $N_2$ atmosphere. 3 was added dropwise to the solution (so as to keep the reaction temperature at −20° C.) and the reaction mixture was stirred for 8 hours at −20° C. under a $N_2$ atmosphere. During the activation (formation of mixed anhydride, reaction 1) the TLC (silica gel) of the reaction mixture was checked by using n-butyl amine.

TLC preparation: A few drops of reaction mixture were reacted with one drop of butyl amine. After 2 minutes, 10% citric acid was added to the butyl amine adduct solution. The resultant mixture was extracted with a small amount of EtOAc. The 1 and the EtOAc layer were spotted and these two samples were overlapped. The plate was developed in 30% of EtOAc/hexane and in 5% MeOH/$CH_2Cl_2$ (with 0.1% HOAc) solvent systems. The disappearance of 1 and the formation of butyl amine adduct was monitored. When 1 was observed, another 5–10% of Piv-Cl were added and the reaction mixture was stirred for another 4 hours at the same condition. Then the TLC was checked again and it was determined that activation was complete.

After activation was complete (at least ~90–95% reaction), a mixture of 5, 6 and 7 was added to the flask. The resultant mixture was stirred for 24 hours at −20° C. under $N_2$ atmosphere. The, coupling reaction was monitored by TLC (silica gel).

TLC preparation: A few drops of reaction mixture were reacted with one drop of butyl amine. After 2 minutes, 10% citric acid was added to the butyl amine adduct solution. The resultant mixture was extracted with small amount of EtOAc. A few drops of reaction mixture were reacted with 10% citric acid. The resultant mixture was extracted with a small amount of EtOAc. These two TLC samples were compared with 5 by developing the plate in 30% of EtOAc/hexane and in 5% MeOH/$CH_2Cl_2$ (with 0.1% HOAc) solvent systems. The sample without butyl amine was the coupling product and the sample with butyl amine was the adduct of butyl amine. When the coupling was complete, there was no butyl amine adduct formation in that TLC sample. Also the disappearance of 5 was checked as the coupling reaction was completed.

After the coupling was complete, 10% citric acid solution was added to the reaction mixture and the reaction mixture was extracted with $CH_2Cl_2$ (3×100 mL). The organic layer was washed with saturated $NaHCO_3$ solution and the organic layer was washed with brine. The organic layer was dried with $MgSO_4$. The $CH_2Cl_2$ filtrate was evaporated to a yellow, foaming solid. The product was isolated by using flash chromatography. The crude was loaded in a minimum amount of $CH_2Cl_2$ to the column and the column was washed with 1 L. of hexane. The column was eluted with 10–40% EtOAc/Hexane. The fractions were monitored by TLC (silica gel, 40% EtOAc/Hexane). After column purification, 1.81 gm (60%) of L-N-Boc-phenylalaninyl L-N-methylphenylalaninyl-L-azetidinyl benzyl ester were obtained; FAB-MS m/z 600 $(M+H)^+$.

EXAMPLE 25

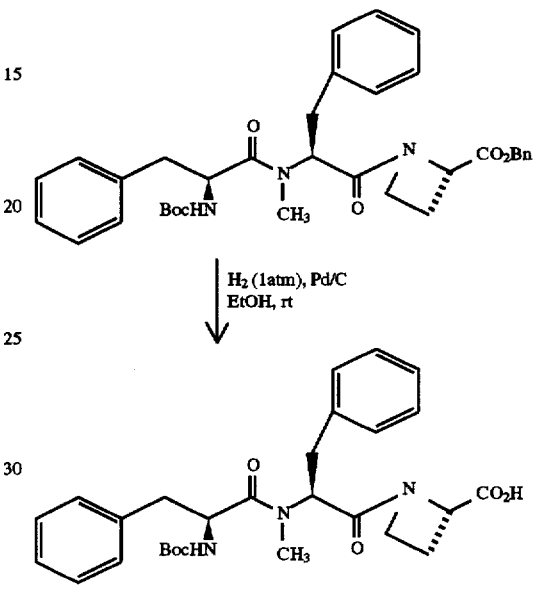

Preparation of L-N-BOC-Phenylalaninyl methylphenylalaninyl L-azetidine

L-N-BOC-phenylalaninyl L-N-methylphenylalaninyl L-azetidinyl benzyl ester (1.8 gm, 3.0 mmol) was dissolved in 50 ml of EtOH under a $N_2$ atmosphere. 10% Palladium on activated carbon was added to the solution. The flask was equipped with a $H_2$ balloon and the flask (under $N_2$) was evacuated using the house vacuum. The $H_2$ to the flask was released and the flask was evacuated. This procedure was repeated twice. The black mixture was stirred under $H_2$ at room temperature overnight (20 hours). The reaction mixture was filtered through celite and the filtrate was evaporated to obtain 1.4 g of white, foaming L-N-BOC-phenylalaninyl L-N-methylphenylalaninyl L-azetidine. The reaction was monitored by the TLC (silica gel, 5% MeOH/$CH_2Cl_2$ with 0.1% HOAc); FAB-MS m/z 510 $(M+H)^+$.

As used in the above example and throughout this specification, rt means room temperature.

EXAMPLE 26

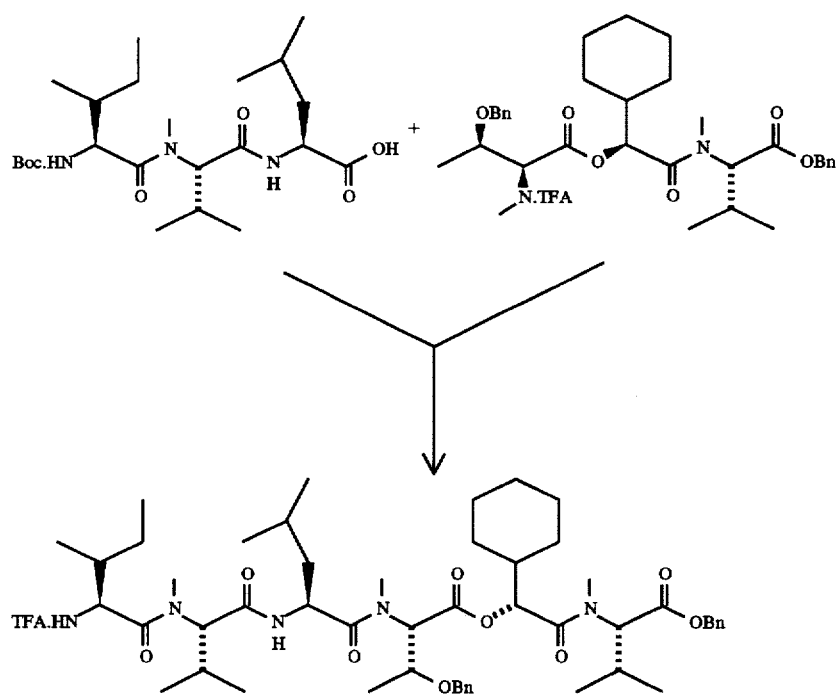

Preparation of Allo-isoleucyl-n-methylvalyl-leucyl-L-O-Bn-threonyl-(R)-hexahydromandelate-L-methylvaline-O-benzyl ester TFA salt Boc-allo-isoleucyl-N-methyl-valyl-leucine (0.83 gm, 1.81 mmole) was dissolved in 20 ml of dry methylene chloride under a dry nitrogen atmosphere. NMM (0.4 ml, 3.62 mmol) was added and the reaction mixture was cooled to −20° C. Pivaloylchloride (0.25 ml, 1.99 mmol) was added and the reaction mixture was stirred for 18 hours at −20° C. In a separate flame dried 100 ml round bottom flask, L-O-Bn-threonyl-(R)-hexahydromandelate-L-methylvaline TFA salt (1.23 gm, 1.81 mmol) was dissolved in 20 ml of dry methylene chloride and 0.23 ml (2.0 mmol) of NMM. This clear solution was added to the above reaction and stirred at −20° C. for 48 hours. The cold bath was removed and, while cold, the reaction mixture was acidified with 10% citric acid to pH=3 to 2.5. The reaction mixture was extracted with 3×100 ml of methylene chloride. The methylene chloride extracts were dried over magnesium sulfate, filtered, and evaporated to dryness. The resulting gum was chromatographed on a flash grade silica column packed in hexanes, eluted with hexanes; followed by 10% ethylacetate/hexanes; followed by 20% ethylacetate/hexanes; followed by 30% ethylacetate/hexanes; followed by 40% ethylacetate/hexanes; and finally 70% ethylacetate/hexanes. The product containing fractions were collected and evaporated to dryness to obtain 1.3 gm of title product which was dissolved in methylene chloride (30 ml) and cooled to 10° C. Trifluoroacetic acid (TFA) (10 ml) was added and the mixture was stirred for 3 hours and evaporated to dryness to give the title compound. FAB-MS m/z 1006 (M+H)$^+$.

EXAMPLE 27

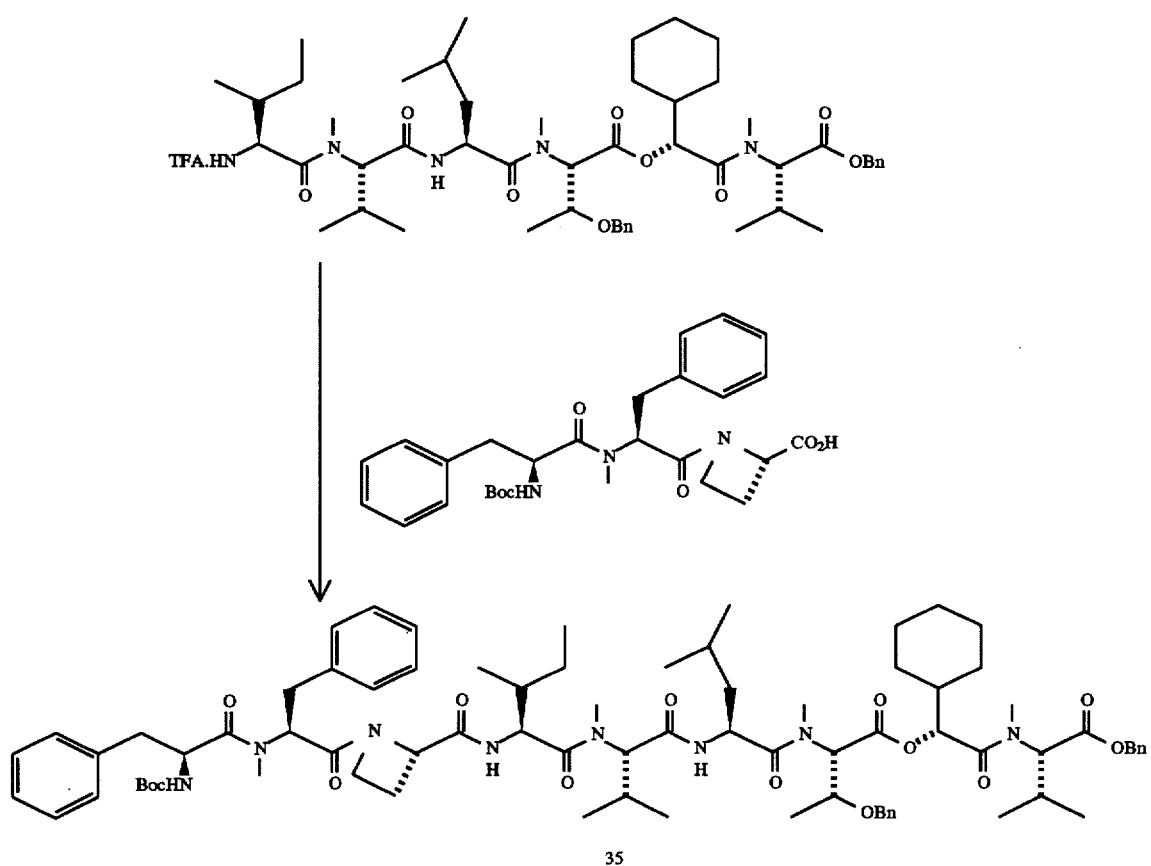

Preparation of N-Boc-phenylalanyl-N-methylphenylalanyl-azetidinyl-allo-isoleucyl-N-methylvalyl-leucyl-L-O-Bn-threonyl-(R)-hexahydromandelate-L-methylvaline-O-benzyl ester L-N-BOC-phenylalaninyl L-N-methylphenylalaninyl L-azetidine (0.949 gm, 1.86 mmol) was dissolved in 50 ml of dry methylene chloride under a dry nitrogen atmosphere. NMM (0.41 ml, 3.75 mmol) was added and the mixture was cooled to −20° C. Pivaloylchloride (0.25 ml, 2.04 mmol) was added and the mixture was stirred for 24 hours at −20° C. In a separate flame dried 100 ml round bottom flask was dissolved alloisoleucyl-N-methyl-valyl-leucine-L-O-Bn-threonyl-(R)-hexahydromandelate-L-methylvaline-O-benzyl ester TFA salt (1.9 gm, 1.86 mmol) in 30 ml of dry methylene chloride and 0.25 ml (2.23 mmol) of NMM. This clear solution was added to the above reaction and the reaction mixture was stirred at 10° C. for 48 hours. The cold bath was removed and, while cold, acidified with 10% citric acid to pH=3 to 2.5. The reaction mixture was extracted with 3×500 ml of methylene chloride. The methylene chloride extracts were dried over magnesium sulfate, filtered, and evaporated to dryness. The resulting gum was chromatographed on a flash grade silica column packed in hexanes. Elution was with hexanes followed by 25% ethylacetate/hexanes; followed by of 30% ethylacetate/hexanes; followed by of 40% ethylacetate/hexanes; followed by of 50% ethylacetate/hexanes; and finally of 70% ethylacetate/hexanes. The product containing fractions were collected and evaporated to dryness to obtain 1.81 gm of title product. FAB-MS m/z 1420 (M+Na)$^+$.

EXAMPLE 28

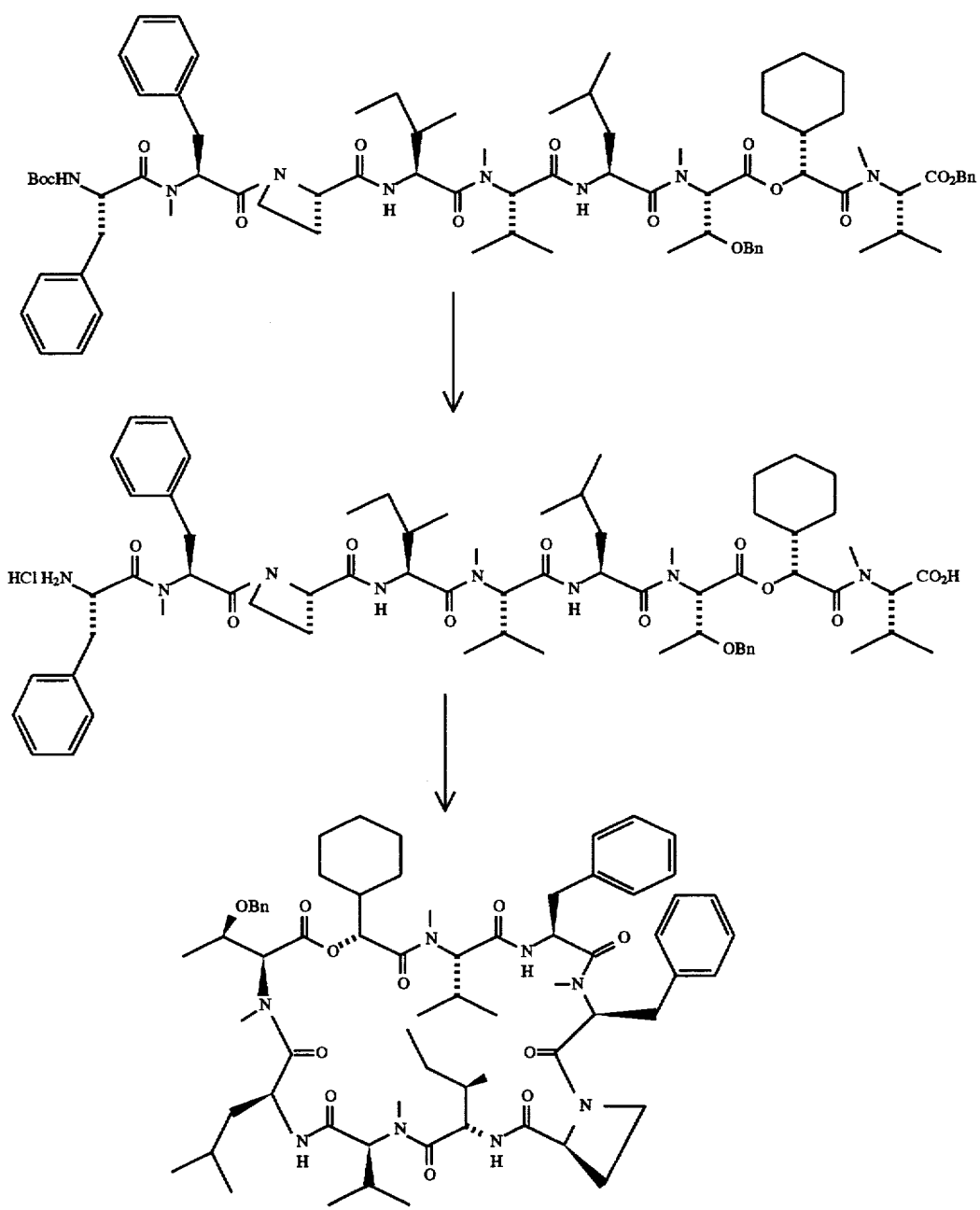

Preparation of Cyclo-depsi-N-methyl-O-benzyl-threonyl-(2-hydroxy-2-cyclohexylacetyl)-N-methylvalyl-phenylalanyl-N-methylphenylalanyl-azetidinyl-allo-isoleucyl-N-methyl-leucine To a solution of the double deprotected depsi-nonapeptide HCl salt (0.5 g, 0.36 mmol, obtained by sequentially treating nonapeptide with 1 atm of $H_2$ over 10% Pd/C (5% w/w), trifluoroacetic acid in $CH_2Cl_2$ at 0° C. then with 1N dry HCl in ether) in 400 ml of dry $CH_2Cl_2$, were added dimethylaminopyridine(0.26 g.) and benzotriazol-1-yloxytris(dimethylamino)phosphonium hexafluorophosphate (0.76 gm). The mixture was stirred for 3 days, then partitioned between 1% citric acid and ethyl acetate. The organic layer was washed with $H_2O$, brine, dried over $Na_2SO_4$ and concentrated. The residue was chromatographed on silica gel (60% ethyl acetate/hexane) to provide O-benzyl-cyclo-depsi-nonapeptide (0.252 g.) as a white solid: FAB-MS m/z 1189 (M+H)$^+$.

EXAMPLE 29

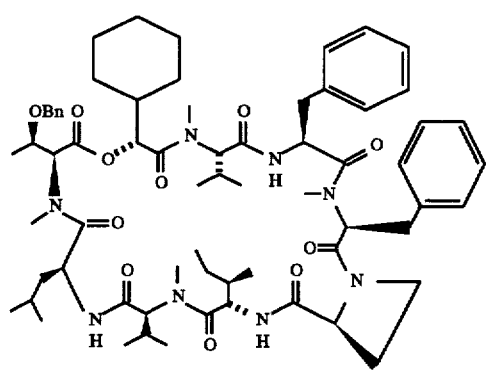

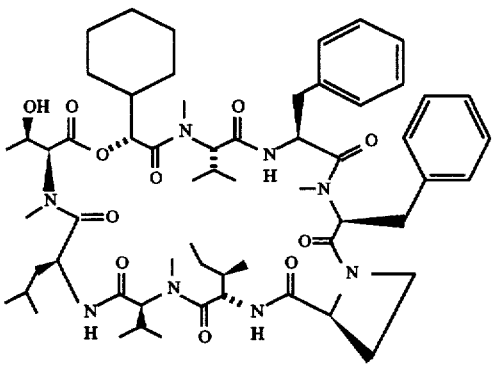

Preparation of Cyclo-depsi-N-methyl-threonyl-(2-hydroxy-2-cyclohexylacetyl)-N-methylvalyl-phenylalanyl-N-methylphenylalanyl-azetidinyl-allo-isoleucyl-N-methylvalyl-leucine The O-benzyl-cyclo-depsi-nonapeptide (200 mg.) in 15 ml of ethanol and 0.35 ml of 1N HCl was hydrogenated (1 atm of $H_2$, 50 mg of 10% Pd/C) for 6 hours. After Pd/C was removed and the solvents were evaporated, the crude product was chromatographed on silica gel (80% ethyl acetate/hexane) to provide cyclo-depsi-nonapeptide (109 mg.) as a white solid: FAB-MS m/z 1099 (M+H)$^+$.

EXAMPLE 30

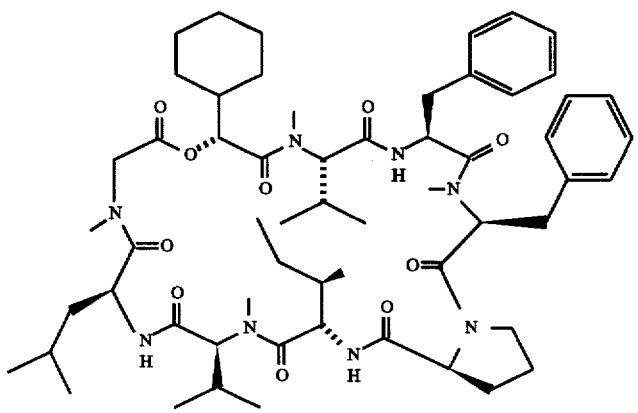

1) 6 eq. LiN(TMS)$_2$
28 eq. LiCl in THF
2) 20 eq. R$_1$R$_2$CO

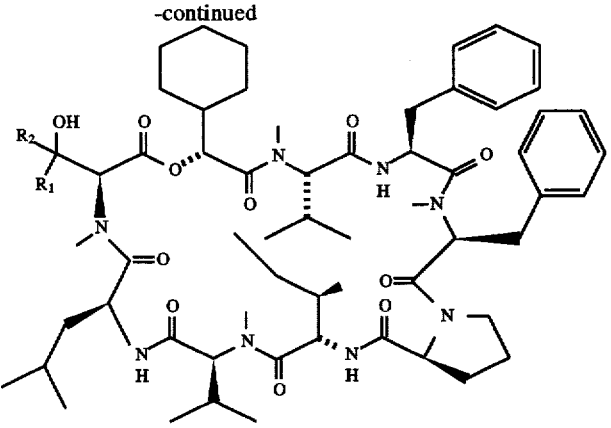
More specifically the following is an example of this reaction and product.
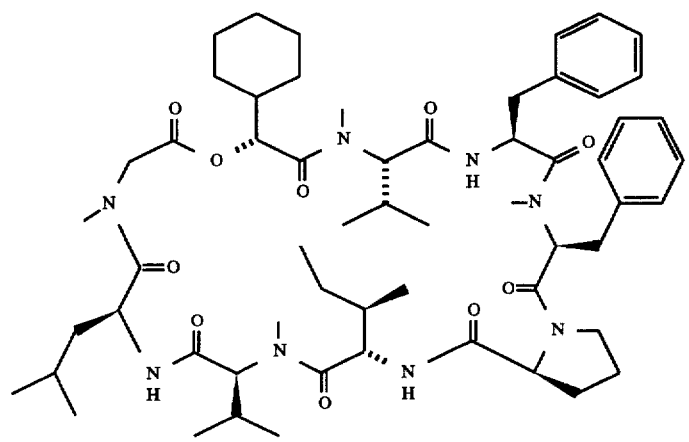
1) 6 eq. Li N(TMS)₂
   28 eq. LiCl in THF
2) 20 eq. CH₃CHO
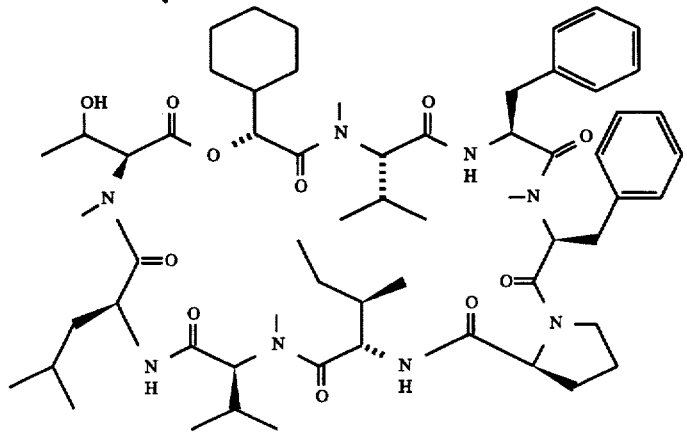

55

Cyclo-depsi-N-methylthreonyl-(2-hydroxyl-3-methylpentanoyl)-N-methylvalyl-phenylanalyl-N-methylphenylanalyl-prolyl-allo-isoleucyl-N-methylvalyl-leucine To a solution of cyclo-depsi-sarcosinyl-(2-hydroxyl-3-methylpentanoyl)-n-methylvalyl-phenylanalyl-n-methylphenylanalyl-prolyl-allo-isoleucyl-N-methylvalyl-leucine (50 mg, 0.047 mmol) in 6 ml of THF was added lithium chloride (57mg, 1.3 mmol). The mixture was cooled to −78° C. under a dry nitrogen atmosphere and a 1M solution of lithium bistrimethylsilylamide (0.27 ml, 0.27 mmol) was added dropwise. After stirring for 4 hours, acetaldehyde (53 μl, 0.94 mmol) was added and the reaction mixture stirred at −50° C. for 3 days. 20 ml of methylene chloride was added and the solution washed with 10% citric acid solution. After chromatography on silica gel using 1% to 5% methanol/methylene chloride 11 mg (22%) of the title product was obtained. FAB-MS m/z 1088 (M+H)$^+$.

EXAMPLE 31

More specifically the following is an example of this reaction and product.

Cyclo-depsi-N-methylthreonyl-(2-hydroxyl-2-cyclohexylacetyl)-N-methylvalyl-phenylanalyl-D-N-methylphenylanalyl-prolyl-allo-isoleucyl-N-methylvalyl-leucine

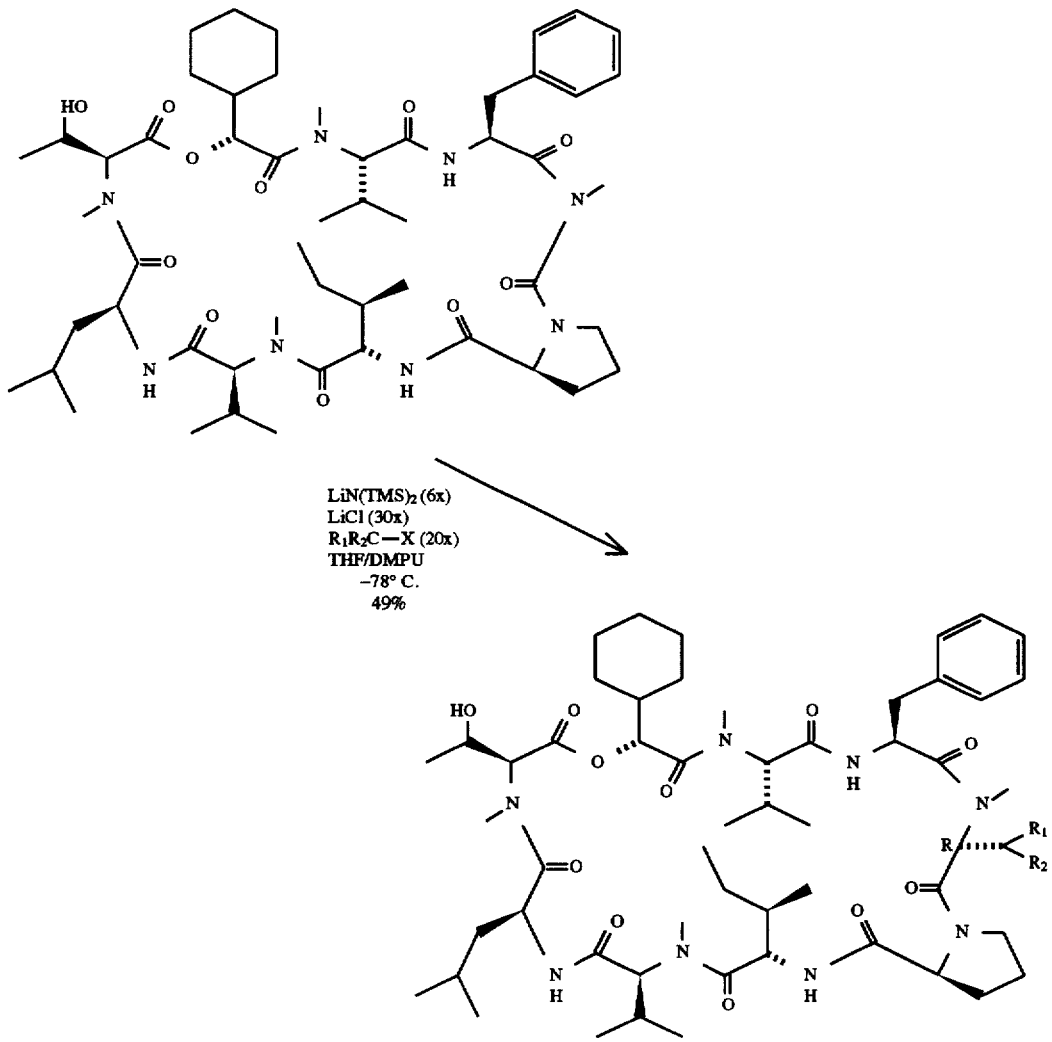

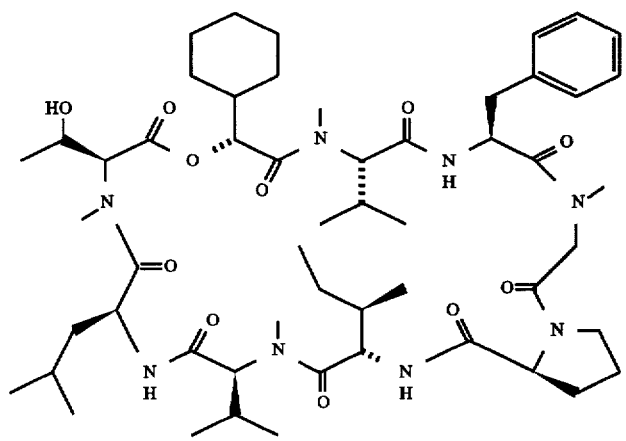

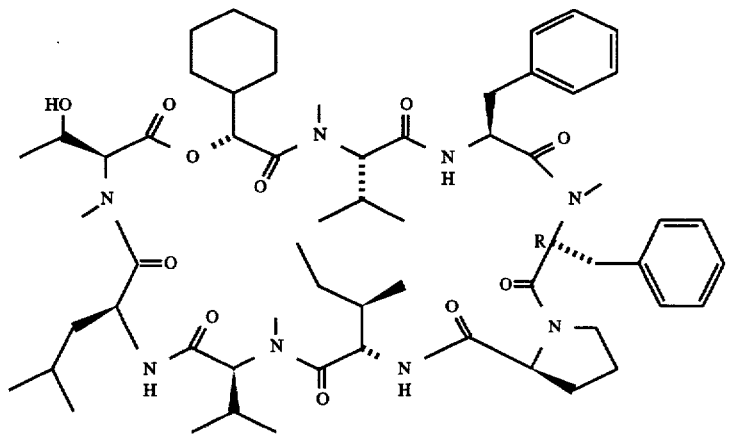

To a solution of 83 mg of the starting non-benzylated compound, (0.081 mmol) and 95 mg of LiCl (2.24 mmol) in 6 ml of THF, 0.45 ml of lithium bis(trimethylsilyl)amide (1M THF solution) was added at −78° C. After stirring for 4 hours, 0.6 ml of DMPU, followed by 0.137 ml of benzylbromide (1.49 mmol) was added at −78° C. The solution was stirred for 3 days at the same temperature. The reaction was quenched by 5 ml of 1M phosphate buffer (pH=7) at −78° C., extracted with ethyl acetate. The organic layer was washed with $H_2O$, dried over $Na_2SO_4$, and concentrated. The residue was separated on a preparative silica gel TLC plate, developed with 50% acetone:/hexane. The resulting benzylated compound was obtained in 44 mg (49% of yield).

NOSEY NMR confirmed the stereochemistry.m/z (FAB), 1113 (MH+).

The starting materials in the above examples are known or can be prepared according to known methods.

The following table illustrates other compounds of formula I of the invention which may be made by using procedures analogous to those set forth above.

Exemplary compounds of the invention include:

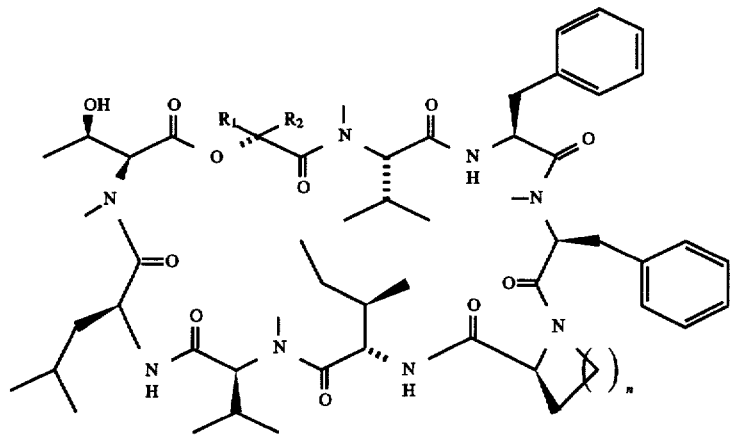

| No. | R₂ | n | Starting Material | M.W. |
|---|---|---|---|---|
| 1 | Cyclohexyl | 2 | R-hexahydromandelic acid | 1113.4 |
| 2 | Cyclohexyl | 1 | R-hexahydromandelic acid | 1099.4 |
| 4 | i-Pr | 2 | 2-(R)-hydroxy-3-Methyl-butanoic acid instead of R-hexahydromandelic acid | 1073.4 |
| 5 | Cyclopentyl | 1 | 2-(R)-2-cyclopentylacetic acid instead of R-hexahydromandelic acid | 1085.4 |
| 6 | Cyclopentyl | 2 | 2-(R)-2-cyclopentylacetic acid instead of hexahydromandelic acid | 1099.4 |
| 7 | Phenyl | 2 | mandelic acid instead of R-hexahydromandelic acid | 1107.4 |
| 8 | Cyclopropyl | 2 | 2-S-hydroxy-2-cyclopropylacetic acid instead of R-hexahydromandelic acid | 1071.3 |
| 9 | Cyclohexyl | 3 | R-hexahydromandelic acid | 1127.4 |

In all of the compounds in the table just above, $R_1$ is H.

What is claimed is:

1. A compound of the formula

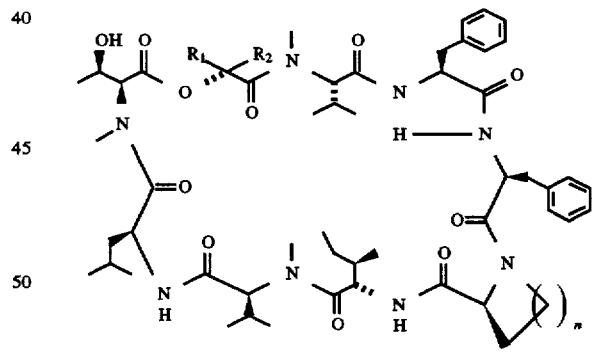

wherein R1 is H, R2 is cyclohexyl and n=3.

2. A compound selected from the group consisting of:

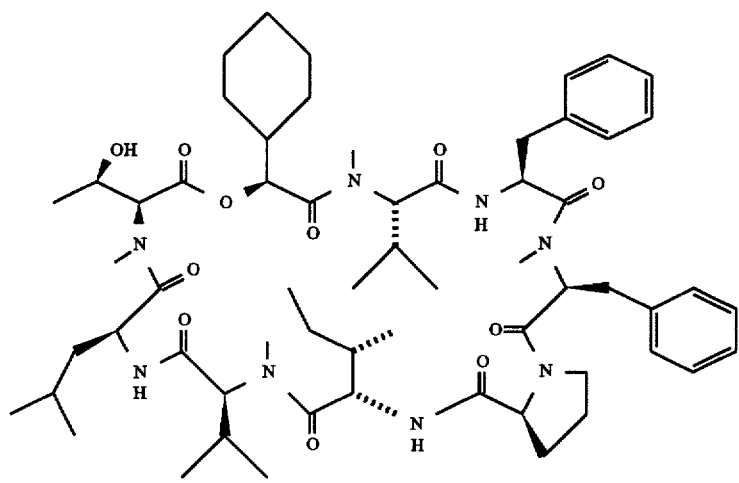
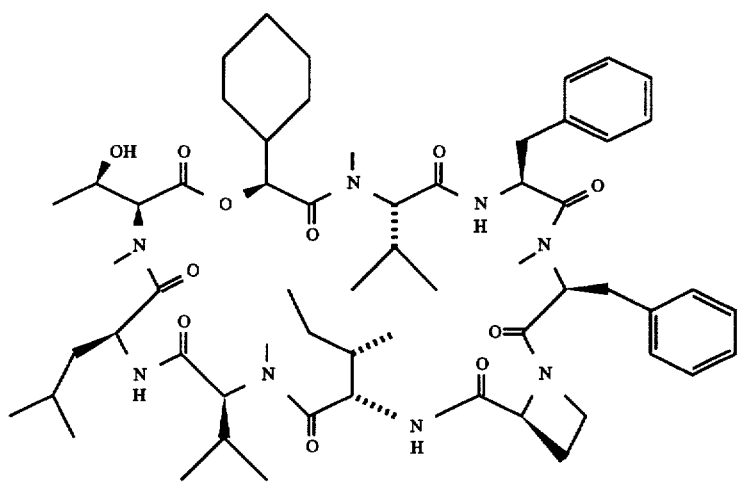
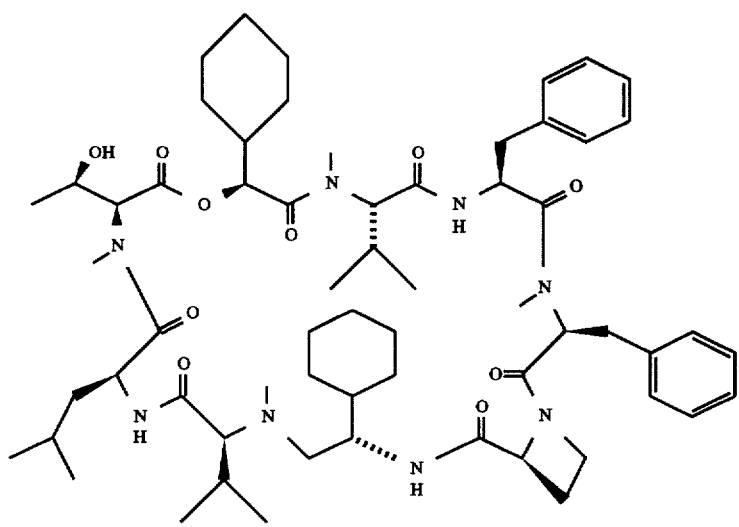

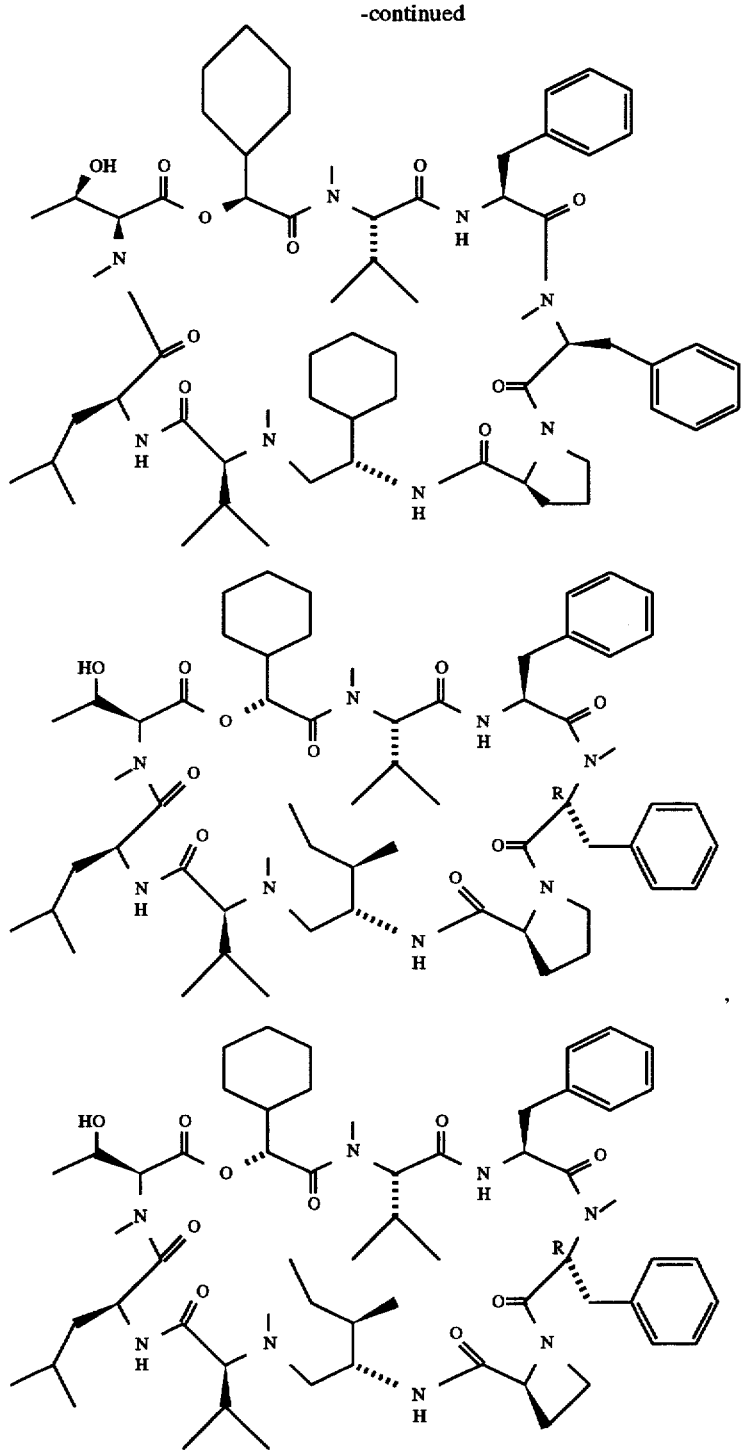

, and

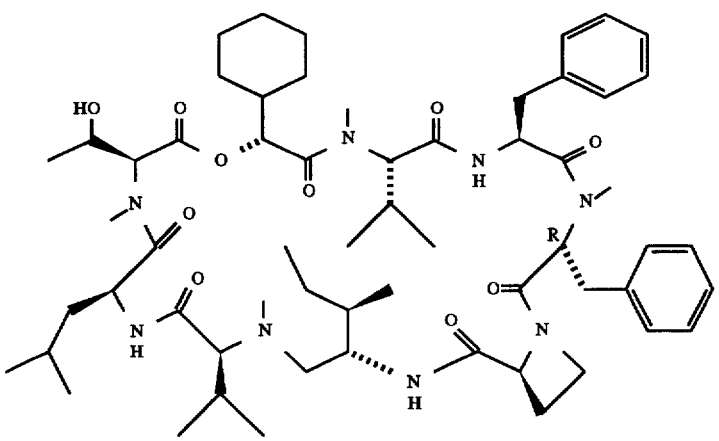

3. A pharmaceutical composition comprising a compound as defined in claim 1 in combination with a pharmaceutically acceptable carrier.

4. A method for treating a fungal infection in a mammal which comprises administering to the mammal an antifungally effective amount of a compound according to claim 1.

5. A pharmaceutical composition comprising a compound as defined in claim 2 in combination with a pharmaceutically acceptable carrier.

6. A method for treating a fungal infection in a mammal which comprises administering to the mammal an antifungally effective amount of a compound according to claim 2.

* * * * *